United States Patent
Yamashita et al.

(10) Patent No.: US 9,606,075 B2
(45) Date of Patent: Mar. 28, 2017

(54) GAS DETECTOR AND PROGRAM

(71) Applicant: NGK SPARK PLUG CO., LTD., Nagoya-shi, Aichi (JP)

(72) Inventors: Masahiro Yamashita, Komaki (JP); Shoji Kitanoya, Kasugai (JP); Masaya Watanabe, Komaki (JP); Daisuke Ichikawa, Kani (JP); Yusuke Matsukura, Nagoya (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 43 days.

(21) Appl. No.: 14/748,975

(22) Filed: Jun. 24, 2015

(65) Prior Publication Data

US 2016/0061756 A1     Mar. 3, 2016

(30) Foreign Application Priority Data

Jun. 30, 2014   (JP) ................................. 2014-134745

(51) Int. Cl.
| G01N 27/18 | (2006.01) |
| G01N 25/18 | (2006.01) |
| G01N 27/14 | (2006.01) |
| G01N 33/00 | (2006.01) |

(52) U.S. Cl.
CPC .............. *G01N 25/18* (2013.01); *G01N 27/14* (2013.01); *G01N 27/18* (2013.01); *G01N 33/005* (2013.01)

(58) Field of Classification Search
CPC ........ G01N 27/04; G01N 27/14; G01N 27/18; G01N 27/045; G01N 27/046; G01N 25/18; G01N 33/0006; G01N 33/005; G01N 33/0036
See application file for complete search history.

(56) References Cited

U.S. PATENT DOCUMENTS

| 2006/0289400 | A1* | 12/2006 | Takahashi | ............ | G01N 33/005 219/121.36 |
| 2014/0053631 | A1* | 2/2014 | Watanabe | ................ | G01N 9/36 73/30.01 |

FOREIGN PATENT DOCUMENTS

JP          2012-181184 A          9/2012

* cited by examiner

*Primary Examiner* — Blake A Tankersley
(74) *Attorney, Agent, or Firm* — Sughrue Mion, PLLC

(57) ABSTRACT

A first bridge fixed resistor (211) of a combustible gas detection apparatus (1) is composed of a resistor element which is less likely to deteriorate as compared with a second bridge fixed resistor (212) and a variable resistor section (213). The combustible gas detection apparatus (1) can judge a deteriorated state of at least one of the second bridge fixed resistor (212) and the variable resistor section (213) on the basis of the absolute value of a difference temperature $\Delta T$ which is the difference between a detection-time judgment temperature T1 and a reference judgment temperature T0. The combustible gas detection apparatus (1) obtains a corrected high-temperature-time voltage VH' and a corrected low-temperature-time voltage VL' through use of a voltage error $\Delta V1$. Thus, a decrease in the accuracy in detecting the hydrogen concentration can be suppressed even when the resistance of the resistor section changes.

10 Claims, 7 Drawing Sheets

GAS DETECTOR AND PROGRAM

TECHNICAL FIELD

The present invention relates to a gas detector and a program which are used for measurement of the concentration of a specific gas, leakage detection, or the like.

BACKGROUND ART

In recent years, in consideration of demand of society, such as environmental protection and nature conservation, researches have been actively conducted on a fuel cell, which is an energy source which is high in efficiency and low in environmental load. Among various types of fuel cells, a polymer electrolyte fuel cell (PEFC) has drawn people's attention as an energy source for home use or an energy source for vehicles because it is advantageous in that its operation temperature is low and its output density is high. Such a polymer electrolyte fuel cell uses, as a fuel, hydrogen which is more likely to leak as compared with other fuels. Therefore, it is considered that a gas detector which detects leakage of hydrogen becomes necessary for practical implementation of the polymer electrolyte fuel cell.

Also, researches have been actively conducted on a hydrogen internal combustion engine which is an energy source which is low in environmental load and which uses hydrogen as a fuel like the polymer electrolyte fuel cell. As to the hydrogen internal combustion engine as well, it is considered that a gas detector which detects leakage of hydrogen becomes necessary for practical implementation.

A gas detector including a heat generation resistor has been known as a gas detector for detecting leakage of a specific gas (e.g., hydrogen) in a to-be-detected atmosphere. This gas detector measures the quantity of heat taken from the heat generation resistor by the to-be-detected atmosphere and calculates a change in the thermal conductivity of the to-be-detected atmosphere to thereby obtain the concentration of the specific gas (hydrogen concentration).

There has been known a gas detector which has a Wheatstone bridge circuit including a heat generation resistor as one of four resistor sections thereof and which measures the quantity of heat taken from the heat generation resistor by the to-be-detected atmosphere through use of the Wheatstone bridge circuit (see, for example, Patent Document 1).

PRIOR ART DOCUMENT

Patent Document

[Patent Document 1] Japanese Patent Application Laid-Open (kokai) No. 2012-181184

SUMMARY OF THE INVENTION

Problem to be Solved by the Invention

However, in the case of the above-described gas detector using a Wheatstone bridge circuit, even when one of the four resistor sections other than the heat generation resistor deteriorates due to, for example, the lapse of time, deterioration of the resistor section cannot be detected.

In the case where a resistor section deteriorates and its resistance changes, there arises a possibility that the accuracy in measuring the quantity of heat taken from the heat generation resistor by the to-be-detected atmosphere decreases and the accuracy in detecting the concentration of a gas decreases.

Namely, in the case where the resistance of one of the four resistor sections of the Wheatstone bridge circuit other than the heat generation resistor changes, the accuracy in detecting the resistance of the heat generation resistor (or the voltage between the opposite ends of the heat generation resistor) decreases. As a result, the accuracy in measuring the quantity of heat taken from the heat generation resistor by the to-be-detected atmosphere decreases, and the accuracy in detecting the concentration of a gas decreases.

An object of the present invention is to provide a gas detector which can detect deterioration of a resistor section provided in a Wheatstone bridge circuit, or provide a gas detector and a program which suppress a decrease in the accuracy in detection of gas concentration even when the resistance of a resistor section provided in the Wheatstone bridge circuit changes.

Means for Solving the Problems

A gas detector according to one aspect of the present invention comprises a heat generation resistor, a Wheatstone bridge circuit, a bridge control section, and a computation section, wherein the computation section comprises a gas concentration computation section, a reference judgment value storage section, a detection-time judgment value computation section, and a deterioration judgment section.

The heat generation resistor is disposed in a to-be-detected atmosphere, and its resistance changes with a change in the own temperature. The Wheatstone bridge circuit is configured by connecting in parallel a first side including the heat generation resistor and a first resistor section connected in series and a second side including a second resistor section and a third resistor section connected in series. The bridge control section controls the state of supply of electricity to the Wheatstone bridge circuit in such a manner that the Wheatstone bridge circuit becomes a balanced state. The computation section computes the concentration of a specific gas in the to-be-detected atmosphere.

The bridge control section includes an operational amplifier having an output terminal and two input terminals. The bridge control section controls the state of supply of electricity to the Wheatstone bridge circuit in accordance with the output of the operational amplifier in such a manner that the potential difference between the two input terminals of the operational amplifier becomes zero.

The Wheatstone bridge circuit is configured to have a reference point, a high potential point, a first potential point, and a second potential point.

The reference point is one of connection points where the first side and the second side are connected together and is connected to one side of the bridge control section which becomes a low potential side when the bridge control section applies a voltage to the Wheatstone bridge circuit.

The high potential point is the other of the connection points where the first side and the second side are connected together and is connected to the other side of the bridge control section which becomes a high potential side when the bridge control section applies the voltage to the Wheatstone bridge circuit.

The first potential point is a connection point where the first resistor section and the heat generation resistor are connected together and is connected to one input terminal of the operational amplifier. The second potential point is a connection point where the second resistor section and the third resistor section are connected together and is connected to the other input terminal of the operational amplifier.

The first resistor section has a characteristic such that a ratio of a change in the resistance due to deterioration with elapse of time or deterioration caused by an environmental load is small as compared with those of the second resistor section and the third resistor section. Notably, the deterioration caused by an environmental load means deterioration caused by the influence of temperature, humidity, energization, etc.

The gas concentration computation section computes the concentration of the specific gas in the to-be-detected atmosphere through use of at least a voltage between opposite ends of the heat generation resistor detected on the basis of the potential at the first potential point. Notably, in the case where the connection point between the heat generation resistor of the first side and the third resistor section of the second side is used as the reference point, the voltage between the first potential point and the reference point corresponds to the voltage between the opposite ends of the heat generation resistor. In this case, when the potential at the reference point is assumed to be a reference potential (=0 V), the potential at the first potential point corresponds to the voltage between the opposite ends of the heat generation resistor.

The reference judgment value storage section stores a reference judgment value. The reference judgment value is determined on the basis of a reference top potential which is a potential at the high potential point and serves as a reference and a reference intermediate potential which is a potential at the first potential point or the second potential point and serves as a reference.

The detection-time judgment value computation section computes a detection-time judgment value on the basis of a detection-time top potential which is a potential at the high potential point and a detection-time potential which is a potential at the first potential point or the second potential point at the time when gas detection is performed by the gas detector.

The deterioration judgment section judges a deteriorated state of at least one of the second resistor section and the third resistor section on the basis of the reference judgment value and the detection-time judgment value.

In the gas detector having the above-described configuration, the first resistor section has a characteristic that it is small in the ratio of a change in resistance due to deterioration as compared with the second and third resistor sections. Therefore, when the resistor sections of the Wheatstone bridge circuit are compared with one another, the second resistor section and the third resistor section become more likely to deteriorate earlier than does the first resistor section.

The reference judgment value is determined by the resistances of the second resistor section and the third resistor section which serve as references, and the detection-time judgment value is determined by the resistances of the second resistor section and the third resistor section at the time of gas detection.

Notably, the reference judgment value may be a reference value which is determined on the basis of, for example, the resistances of the second resistor section and the third resistor section in a stage before shipment of the gas detector.

Therefore, in the case where both the second resistor section and the third resistor section remain undeteriorated at the time of gas detection, the resistances of the second resistor section and the third resistor section at the time of gas detection do not differ greatly from the resistances of the second resistor section and the third resistor section which serve as references. Therefore, the detection-time judgment value assumes a value approximately the same as the reference judgment value. In this case, the difference between the reference judgement value and the detection-time judgment value is small, or the ratio between the reference judgement value and the detection-time judgment value assumes a value close to 1.0.

Meanwhile, in the case where at least one of the second resistor section and the third resistor section is in a deteriorated state at the time of gas detection, the resistance of at least one of the second resistor section and the third resistor section at the time of gas detection changes to a value corresponding to the deteriorated state. Therefore, the detection-time judgment value assumes a value different from the reference judgment value. In this case, the difference between the reference judgement value and the detection-time judgment value is large, or the ratio between the reference judgement value and the detection-time judgment value assumes a value deviating far from 1.0 (a value sufficiently larger than 1.0 or a value sufficiently smaller than 1.0).

Therefore, the deterioration judgement section can judge the deteriorated state of at least one of the second resistor section and the third resistor section on the basis of the reference judgement value and the detection-time judgement value. For example, the deterioration judgement section can judge the deteriorated state on the basis of the difference between the reference judgement value and the detection-time judgement value or the ratio between the reference judgement value and the detection-time judgement value.

Accordingly, the gas detector of the present invention can detect deterioration of the resistor sections provided in the Wheatstone bridge circuit.

A gas detector according to another aspect of the present invention comprises a heat generation resistor, a Wheatstone bridge circuit, a bridge control section, and a computation section, wherein the computation section comprises a gas concentration computation section, a reference judgment value storage section, a detection-time judgment value computation section, and a voltage correction section.

The heat generation resistor is disposed in a to-be-detected atmosphere, and its resistance changes with a change in the own temperature. The Wheatstone bridge circuit is configured by connecting in parallel a first side including the heat generation resistor and a first resistor section connected in series and a second side including a second resistor section and a third resistor section connected in series. The bridge control section controls the state of supply of electricity to the Wheatstone bridge circuit in such a manner that the Wheatstone bridge circuit becomes a balanced state. The computation section computes the concentration of a specific gas in the to-be-detected atmosphere.

The bridge control section includes an operational amplifier having an output terminal and two input terminals. The bridge control section controls the state of supply of electricity to the Wheatstone bridge circuit in accordance with the output of the operational amplifier in such a manner that the potential difference between the two input terminals of the operational amplifier becomes zero.

The Wheatstone bridge circuit is configured to have a reference point, a high potential point, a first potential point, and a second potential point.

The reference point is one of connection points where the first side and the second side are connected together and is connected to one side of the bridge control section which becomes a low potential side when the bridge control section applies a voltage to the Wheatstone bridge circuit.

The high potential point is the other of the connection points where the first side and the second side are connected together and is connected to the other side of the bridge control section which becomes a high potential side when the bridge control section applies the voltage to the Wheatstone bridge circuit.

The first potential point is a connection point where the first resistor section and the heat generation resistor are connected together and is connected to one input terminal of the operational amplifier. The second potential point is a connection point where the second resistor section and the third resistor section are connected together and is connected to the other input point of the operational amplifier.

The first resistor section has a characteristic such that a ratio of a change in the resistance due to deterioration with elapse of time or deterioration caused by an environmental load is small as compared with those of the second resistor section and the third resistor section. Notably, the deterioration caused by an environmental load means deterioration caused by the influence of temperature, humidity, energization, etc.

The gas concentration computation section computes the concentration of the specific gas in the to-be-detected atmosphere through use of at least a voltage between opposite ends of the heat generation resistor detected on the basis of the potential at the first potential point. Notably, in the case where the connection point between the heat generation resistor of the first side and the third resistor section of the second side is used as the reference point, the voltage between the first potential point and the reference point corresponds to the voltage between the opposite ends of the heat generation resistor. In this case, when the potential at the reference point is assumed to be a reference potential (=0 V), the potential at the first potential point corresponds to the voltage between the opposite ends of the heat generation resistor.

The reference judgment value storage section stores a reference judgment value. The reference judgment value is determined on the basis of a reference top potential which is a potential at the high potential point and serves as a reference and a reference intermediate potential which is a potential at the first potential point or the second potential point and serves as a reference.

The detection-time judgment value computation section computes a detection-time judgment value on the basis of a detection-time top potential which is a potential at the high potential point and a detection-time potential which is a potential at the first potential point or the second potential point at the time when gas detection is performed by the gas detector.

The voltage correction section corrects the voltage between the opposite ends of the heat generation resistor on the basis of the reference judgment value and the detection-time judgment value.

In the gas detector having the above-described configuration, the first resistor section has a characteristic that it is small in the ratio of a change in resistance due to deterioration as compared with the second and third resistor sections. Therefore, when the resistor sections of the Wheatstone bridge circuit are compared with one another, the second resistor section and the third resistor section deteriorate early as compared with the first resistor section.

The reference judgment value is determined by the resistances of the second resistor section and the third resistor section which serve as references, and the detection-time judgment value is determined by the resistances of the second resistor section and the third resistor section at the time of gas detection.

Notably, the reference judgment value may be a reference value which is determined on the basis of, for example, the resistances of the second resistor section and the third resistor section in a stage before shipment of the gas detector.

Therefore, in the case where both the second resistor section and the third resistor section remain undeteriorated at the time of gas detection, the resistances of the second resistor section and the third resistor section at the time of gas detection do not differ greatly from the resistances of the second resistor section and the third resistor section which serve as references. Therefore, the detection-time judgment value assumes a value approximately the same as the reference judgment value. In this case, the difference between the reference judgement value and the detection-time judgment value is small, or the ratio between the reference judgement value and the detection-time judgment value assumes a value close to 1.0. In this case, the voltage between the opposite ends of the heat generation resistor (in other words, the potential difference between the first potential point and the reference point) assumes a proper value corresponding to the concentration of the specific gas.

Meanwhile, in the case where at least one of the second resistor section and the third resistor section is in a deteriorated state at the time of gas detection, the resistance of at least one of the second resistor section and the third resistor section at the time of gas detection changes to a value corresponding to the deteriorated state. Therefore, the detection-time judgment value assumes a value different from the reference judgment value. In this case, the difference between the reference judgement value and the detection-time judgment value is large, or the ratio between the reference judgement value and the detection-time judgment value assumes a value deviating far from 1.0 (a value sufficiently larger than 1.0 or a value sufficiently smaller than 1.0). In this case, since the voltage between the opposite ends of the heat generation resistor (in other words, the potential difference between the first potential point and the reference point) changes as a result of the influence of the deteriorated state of the resistor section, the voltage assumes a value different from the proper value corresponding to the concentration of the specific gas.

Since the amount of a change in the voltage between the opposite ends of the heat generation resistor changes in accordance with the deteriorated state of the resistor section, the voltage correction section can correct the voltage between the opposite ends of the heat generation resistor on the basis of the reference judgment value and the detection-time judgment value such that the influence of the deteriorated state of the resistor section decreases.

As a result, when the gas concentration computation section computes the concentration of the specific gas through use of the voltage between the opposite ends of the heat generation resistor, the gas concentration computation section can compute the concentration of the specific gas while mitigating the influence of the deteriorated state of the resistor section.

Therefore, the gas detector of the present invention can suppress a decrease in the accuracy in detecting the gas concentration even when the resistance of the resistor section provided in the Wheatstone bridge circuit changes.

Next, in the gas detector including the above-described voltage correction section, the computation section may include a deterioration judgment section which judges a deteriorated state of at least one of the second resistor section and the third resistor section on the basis of the reference judgment value and the detection-time judgment value.

The gas detector including such a deterioration judgment section can detect deterioration of the resistor section provided in the Wheatstone bridge circuit.

Namely, this gas detector can suppress a decrease in the accuracy in detecting the gas concentration even when the resistance of the resistor section provided in the Wheatstone bridge circuit changes, and can detect deterioration of the resistor section provided in the Wheatstone bridge circuit.

Next, the gas detector including the above-described voltage correction section may further comprise a temperature measurement resistor whose resistance changes with a change in an environmental temperature which is the temperature of the to-be-detected atmosphere, wherein the gas concentration computation section computes the concentration of the specific gas through use of not only the voltage between the opposite ends of the heat generation resistor but also the environmental temperature detected through use of the temperature measurement resistor.

Since the concentration of the specific gas is computed through use of the environmental temperature in addition to the voltage between the opposite ends of the heat generation resistor as described above, it is possible to compute the concentration of the specific gas while suppressing the influence of a change in the environmental temperature, whereby the accuracy in detecting the concentration of the specific gas can be improved.

Next, in the above-described gas detector, the computation section may include an obtainment section which obtains the potential at the first potential point, and the potential at the first potential point obtained by the obtainment section may be used for the computation of the concentration of the specific gas by the gas concentration computation section and the computation of the detection-time judgment value by the detection-time judgment value computation section.

Namely, in this gas detector, the potential at the first potential point and the potential at the second potential point are controlled by the bridge control section such that the two potentials become equal to each other. Also, the voltage between the first potential point and the reference point can be detected on the basis of the voltage between the opposite ends of the heat generation resistor. Notably, since the potential at the reference point is the potential at one end of the heat generation resistor, the potential at the first potential point corresponds to the voltage between the opposite ends of the heat generation resistor.

Therefore, even though the gas detector has a simple configuration which includes only the obtainment section for obtaining the potential at the first potential point rather than having a complex configuration which includes signal paths for individually detecting the potential at the first potential point, the potential at the second potential point, and the voltage between the opposite ends of the heat generation resistor, the obtained value can be utilized as the potential at the second potential point and the voltage between the opposite ends of the heat generation resistor.

Therefore, according to this gas detector, it is possible to judge whether or not the heat generation resistor has deteriorated and improve the accuracy in detecting concentration of the specific gas while employing a simple configuration.

Next, in the above-described gas detector, the computation section may include a reference judgment value computation section which computes the reference judgment value on the basis of the reference top potential and the reference intermediate potential.

Namely, the gas detector may be configured such that, instead of the reference judgment value being stored in the reference judgment value storage section in advance, the reference judgment value is computed by the reference judgment value computation section and is stored in the reference judgment value storage section.

For example, the reference judgment value computation section may compute the reference judgment value in a stage before shipment of the gas detector. In this case, a value corresponding to the reference top potential and the reference intermediate potential in the stage before shipment of the gas detector is set as the reference judgment value. In other words, a value corresponding to the reference top potential and the reference intermediate potential in a state in which none of the second resistor section and the third resistor section has deteriorated is set as the reference judgment value.

This improves the judgement accuracy of judging the deteriorated state of at least one of the second resistor section and the third resistor section on the basis of the reference judgment value and the detection-time judgment value.

A program according to another aspect of the present invention may cause a computer to function as the computation section of the above-described gas detector.

When a computer is caused to execute such a program, the computer achieves actions and effects similar to those of the above-described gas detector. Also, the program can be distributed through a network or the like, and replacement of the program in the computer is easier than replacement of components. Accordingly, the function of the gas detector can be readily improved.

This program can be used by storing in, for example, in a computer-readable recording medium, and causing a computer to execute the stored program. Notably, the recording medium may be a portable recording medium or a recording medium incorporated into the computer in advance. Also, this program may be a program which is loaded on a computer through a network.

Effects of the Invention

The gas detector of the present invention can detect deterioration of a resistor section provided in a Wheatstone bridge circuit.

Also, the gas detector of the present invention can suppress a decrease in the accuracy in detecting the gas concentration even when the resistance of the resistor section provided in the Wheatstone bridge circuit changes.

Further, the program of the present invention yields actions and effects similar to those of the above-described gas detector.

MODES FOR CARRYING OUT THE INVENTION

An embodiment to which the present invention is applied will now be described with reference to the drawings.

Notably, the present invention is not limited to the following embodiment, and various forms may be employed so long as they fall within the technical scope of the present invention.

1. First Embodiment 1-1. Overall Configuration

A combustible gas detection apparatus 1 which detects the concentration of hydrogen gas which is a combustible gas contained in a to-be-detected atmosphere will be described as a first embodiment.

The combustible gas detection apparatus 1 is a heat-conduction-type gas detector, and is disposed in, for example, the cabin of a fuel cell automobile for the purpose of, for example, detecting leakage of hydrogen.

Figure 1:
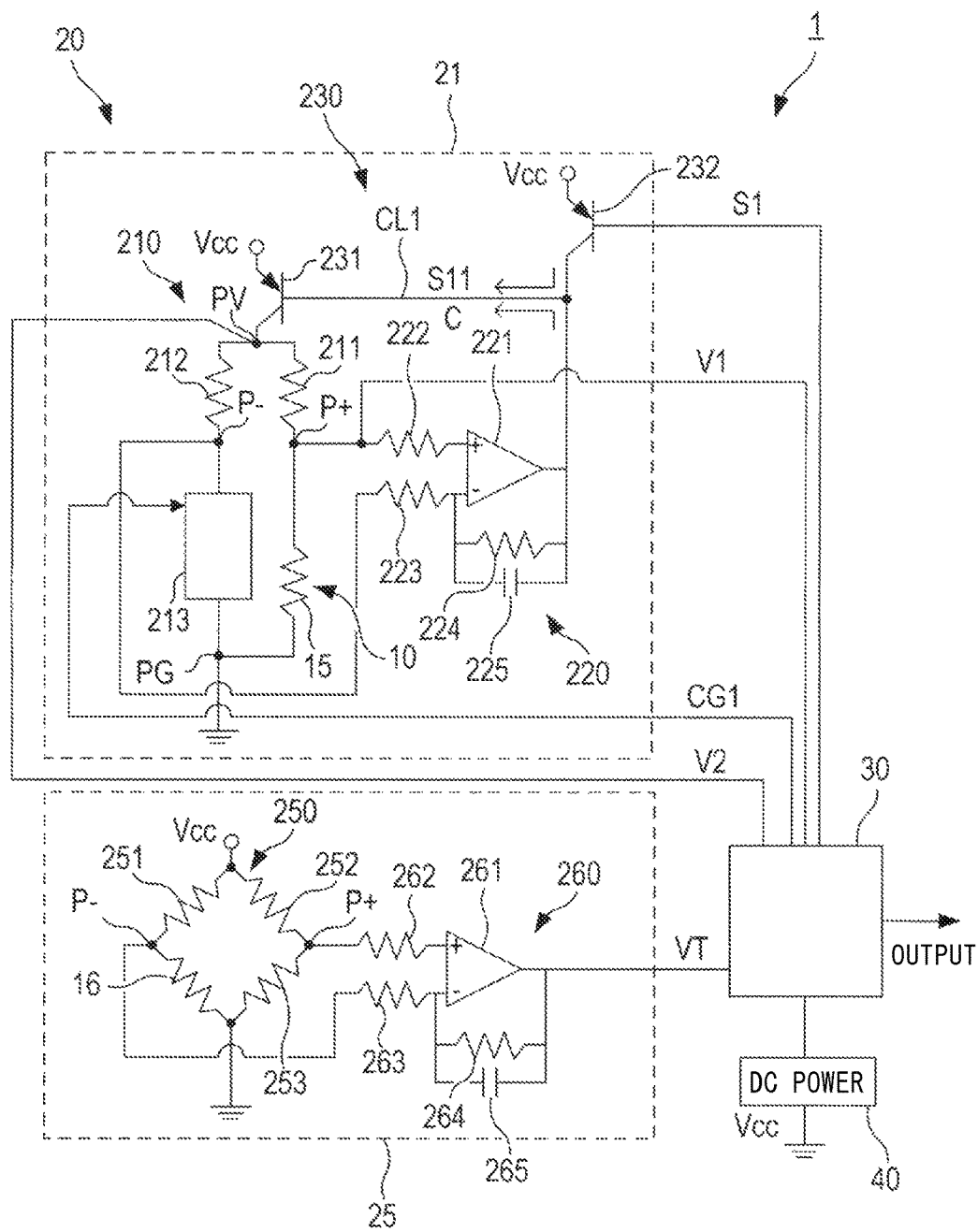
FIG. 1 Diagram describing the overall configuration of a combustible gas detection apparatus.

FIG. 1 is a diagram describing the overall configuration of the combustible gas detection apparatus 1.

The combustible gas detection apparatus 1 is mainly composed of a gas detection element 10 for detecting the concentration of hydrogen gas; a control section 20 for controlling the gas detection element 10; a computation section 30 for executing at least processing of computing the concentration of hydrogen gas on the basis of an output signal of the gas detection element 10; and a DC power supply 40 for supplying electric power to the control section 20 and the computation section 30.

The gas detection element 10 is disposed in such a manner that its back surface on which a recess 13 is formed is exposed to the to-be-detected atmosphere. As shown in a plan view of FIG. 2A and a cross sectional view of FIG. 2B taken along A-A line of FIG. 2A, the gas detection element 10 mainly includes a base 11 formed into the shape of a flat plate; a plurality of electrodes 12 disposed on one surface (hereinafter referred to as the "front surface") of the base 11; and the recess 13 formed on the other surface (hereinafter referred to as the "back surface") of the base 11.

The base 11 constitutes the main body of the gas detection element 10 and is a rectangular plate member mainly formed of silicon. The base 11 is a rectangular plate member having a size of several millimeters in length and width (in the present embodiment, a size of about 3 mm×3 mm). An example of a technique for forming the plurality of electrodes and the recess 13 on the base 11 is a micromachining technique (micromachining process) performed for silicon substrates.

The base 11 is composed of a silicon substrate 111 mainly formed of silicon and an insulating layer 112 formed on the front surface of the silicon substrate 111. At the center of the silicon substrate 111, the silicon substrate 111 is removed to form the recess 13 having a square shape in a plan view. On the back surface side of the silicon substrate 111, the insulating layer 112 is exposed through the recess 13. In other words, the base 11 is formed to have a diaphragm structure in which the silicon substrate 111 serves as a frame and the insulating layer 112 serves a membrane.

In a region of the insulating layer 112 corresponding to the recess 13, a line-shaped heat generation resistor 15 is embedded to form a spiral shape. In a region of a peripheral edge portion of the insulating layer 112 located on the upper side in FIG. 2A, a temperature measurement resistor 16 for measuring the temperature of the to-be-detected atmosphere is embedded.

Since the base 11 has the above-described recess 13, a space is formed below a portion of the insulating layer 112 where the heat generation resistor 15 is provided. As a result, the heat generation resistor 15 is thermally isolated from the surroundings (the silicon substrate 111, etc.). Therefore, the temperature of the heat generation resistor 15 can be increased or decreased within a short period of time, whereby the electric power consumed by the heat generation resistor 15 can be reduced.

Notably, the insulating layer 112 may be formed of a single material or formed through use of different materials to have a multi-layer structure. Also, examples of an insulating material used to form the insulating layer 112 include silicon oxide ($SiO_2$) and silicon nitride ($Si_3N_4$).

The heat generation resistor 15 is formed of an electrically conductive material whose resistance changes with a change in the temperature of itself and which has a large temperature coefficient of resistance. The temperature measurement resistor 16 is formed of an electrically conductive material whose electric resistance changes in proportion to the temperature. In the present embodiment, the temperature measurement resistor 16 is formed of an electrically conductive material whose resistance increases as the temperature rises.

The heat generation resistor 15 and the temperature measurement resistor 16 may be formed of the same material. In the present embodiment, the heat generation resistor 15 and the temperature measurement resistor 16 are formed of platinum (Pt).

When the resistance of the temperature measurement resistor 16 changes with the temperature in a state in which a constant current is supplied thereto, the voltage between opposite ends of the temperature measurement resistor 16 (the potential difference between the opposite ends) changes. A voltage obtained by amplifying the voltage between the opposite ends of the temperature measurement resistor 16 is output as a temperature detection signal VT which will be described later. This temperature detection signal VT assumes a reference value (a predetermined potential difference) when the temperature of the to-be-detected atmosphere to which the gas detection element 10 is exposed is a reference temperature set in advance.

Figure 2A:
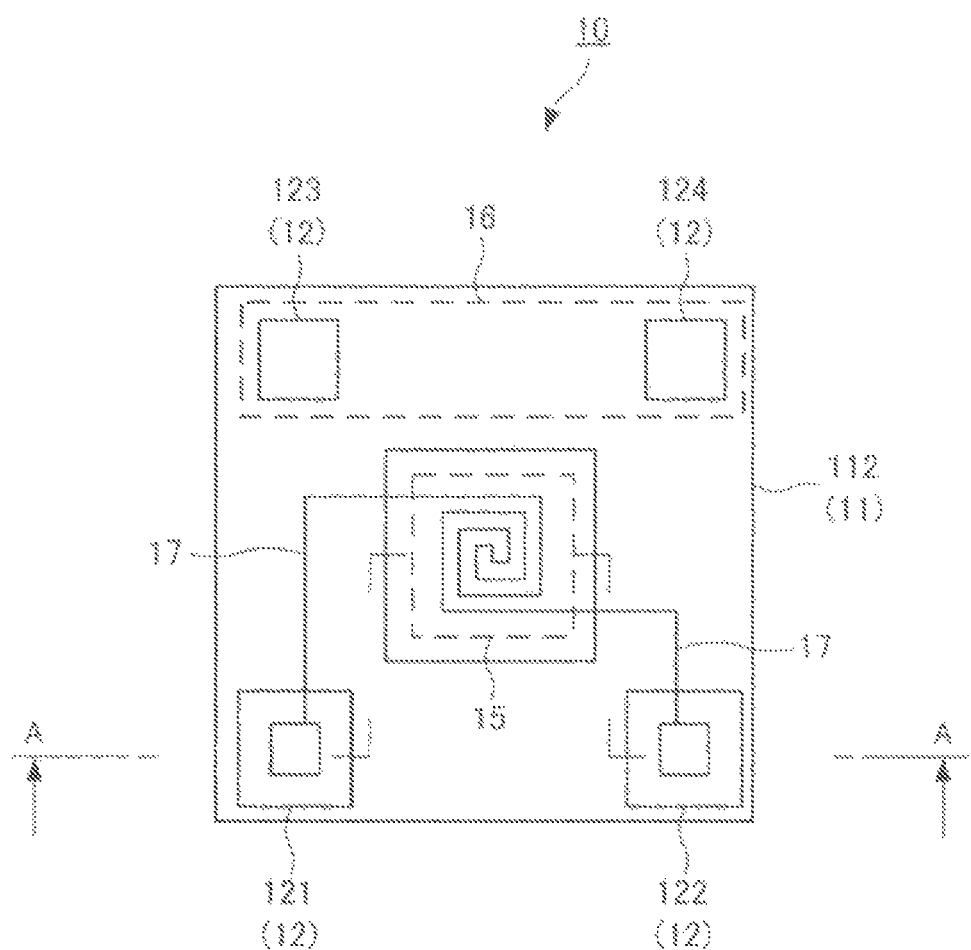
FIG. 2A Plan view describing the structure of a gas detection element.
Figure 2B:
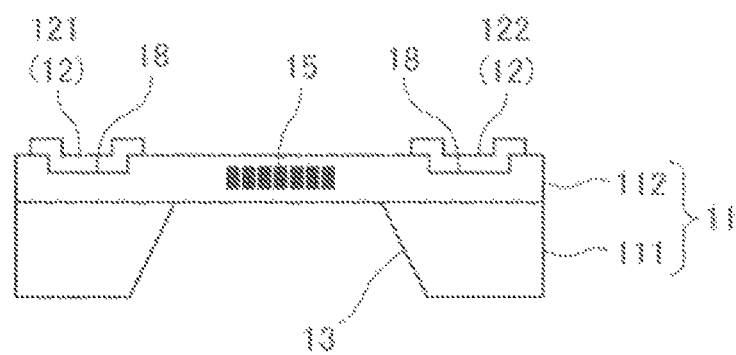
FIG. 2B Cross-sectional view describing the structure of a gas detection element taken along line A-A of FIG. 2A.

The electrodes 12 are four electrodes formed on the front surface of the base 11 at respective positions near the four apexes of the rectangle, and are formed of aluminum (Al) or gold (Au). Of the electrodes 12, two electrodes disposed on the lower side in FIG. 2A are a first electrode 121 and a first ground electrode 122, and two electrodes disposed on the upper side in FIG. 2A are a second electrode 123 and a second ground electrode 124.

Notably, the first electrode 121 is connected to a connection point P+ of an energization control circuit 21 which will be described later, and the second electrode 123 is connected to a connection point P− of a temperature adjustment circuit 25 which will be described later. Both the first ground electrode 122 and the second ground electrode 124 are connected to a ground line which is shared by the control section 20.

Wiring lines 17 and wiring films 18 are provided in the base 11 (specifically, in the insulating layer 112). The wiring lines 17 and the wiring films 18 electrically connect the heat generation resistor 15 to the first electrode 121 and the first ground electrode 122. The first electrode 121 and the first ground electrode 122 formed on the front surface of the base 11 are electrically connected to the wiring films 18 formed in the insulating layer 112 through electrically conductive contact holes. In other words, the heat generation resistor 15 is electrically connected to the first electrode 121 at one end, and is electrically connected to the first ground electrode 122 at the other end.

Notably, the same material as the material used to form the heat generation resistor 15 may be used to form the wiring lines 17 and the wiring films 18.

Also, wiring films (not shown) for electrically connecting the temperature measurement resistor 16 to the second electrode 123 and the second ground electrode 124 are provided in the insulating layer 112. In other words, the temperature measurement resistor 16 is electrically connected to the second electrode 123 at one end and is electrically connected to the second ground electrode 124 at the other end.

Notably, the same material as the material used to form the temperature measurement resistor 16 may be used to form the wiring film for electrically connecting the temperature measurement resistor 16 and the second electrode 123 and to form the wiring film for electrically connecting the temperature measurement resistor 16 and the second ground electrode 124.

1-2. Control Section

Referring back to FIG. 1, the energization control circuit 21 and the temperature adjustment circuit 25 are provided in the control section 20.

The energization control circuit 21 controls the supply of electricity to the heat generation resistor 15. Also, the energization control circuit 21 outputs a detection signal V1 corresponding to the voltage between the opposite ends (inter-terminal voltage) of the heat generation resistor 15, and outputs a TOP voltage signal V2 corresponding to the potential at a connection end portion PV where the first bridge fixed resistor 211 and the second bridge fixed resistor 212 are connected.

Notably, the detection signal V1 also serves as a first intermediate potential signal V3 corresponding to the potential at the connection point P+ at which the first bridge fixed resistor 211 and the heat generation resistor 15 are connected.

The temperature adjustment circuit 25 supplies electricity to the temperature measurement resistor 16. Also, the temperature adjustment circuit 25 outputs a temperature detection signal VT regarding the temperature of the to-be-detected atmosphere.

Also, as will be described later, the potential at the connection point P+ between the first bridge fixed resistor 211 and the heat generation resistor 15 and the potential at the connection point P− between the second bridge fixed resistor 212 and the variable resistor section 213 are controlled by feedback control performed by an amplification circuit 220 and a current adjustment circuit 230 in such a manner that the two potentials become the same. The connection point P+ and the connection point P− are connected to the non-inverting and inverting input terminals, respectively, of an operational amplifier 221 and are virtually shorted. For this reason as well, the two potentials are the same. Therefore, the detection signal V1 not only serves as the first intermediate potential signal V3 corresponding to the potential at the connection point P+ between the first bridge fixed resistor 211 and the heat generation resistor 15 but also serves as a second intermediate potential signal V4 corresponding to the potential at the connection point P− between the second bridge fixed resistor 212 and the variable resistor section 213.

The energization control circuit 21 is a circuit for maintaining the temperature of the heat generation resistor 15 at a predetermined temperature. The energization control circuit 21 includes a bridge circuit 210 which is a Wheatstone bridge circuit including the heat generation resistor 15; the amplification circuit 220 which amplifies the potential difference detected by the bridge circuit 210; and the current adjustment circuit 230 which adjusts (increases or decreases) the current flowing to the bridge circuit 210 in accordance with the output of the amplification circuit 220.

The bridge circuit 210 is a Wheatstone bridge circuit which includes the heat generation resistor 15, the first bridge fixed resistor 211, the second bridge fixed resistor 212, and the variable resistor section 213 whose resistance can be switched. The bridge circuit 210 is composed of a first-side circuit and a second-side circuit which are connected in parallel to each other. The first-side circuit includes the heat generation resistor 15 and the first bridge fixed resistor 211 connected in series, and the second-side circuit includes the second bridge fixed resistor 212 and the variable resistor section 213 connected in series.

The first bridge fixed resistor 211 is connected in series to the heat generation resistor 15. Of end portions of the heat generation resistor 15, the end portion PG opposite the end portion connected to the first bridge fixed resistor 211 is grounded. Of end portions of the first bridge fixed resistor 211, the end portion PV connected to the second bridge fixed resistor 212 is connected to the current adjustment circuit 230 (specifically, a constant temperature control circuit 231). Notably, in the case where one end of the heat generation resistor is connected to the reference point, the potential at the one end of the heat generation resistor becomes equal to the potential at the reference point. Therefore, the potential at the first potential point corresponds to the voltage between the opposite ends of the heat generation resistor.

Notably, the first bridge fixed resistor 211 is composed of a resistor element which is less likely to deteriorate as compared with the second bridge fixed resistor 212 and the variable resistor section 213 (in other words, a resistor element having a characteristic that the ratio of a change in the resistance due to deterioration with lapse of time and deterioration caused by environmental load (deterioration caused by the influence of temperature, humidity, energization, or the like)).

In the present embodiment, there is used a resistor element whose resistance change ratio is 0.5% or less in a high-temperature/high-humidity load test (a load test in which an operation of supplying one tenth of the rated power to the resistor element for 90 minutes and stopping the supply of the power for 30 minutes is repeated for 1,000 hours in an environment whose temperature is 85° C. and whose humidity is 85% RH).

Also, the second bridge fixed resistor 212 is connected in series to the variable resistor section 213. Of end portions of the variable resistor section 213, the end portion PG opposite the end portion connected to the second bridge fixed resistor 212 is grounded. Of end portions of the second bridge fixed resistor 212, the end portion PV connected to the first bridge fixed resistor 211 is connected to the current adjustment circuit 230 (specifically, the constant temperature control circuit 231).

The connection point P+ between the first bridge fixed resistor 211 and the heat generation resistor 15 is connected to the non-inverting input terminal of the operational amplifier 221 through a first fixed resistor 222. The potential at the connection point P+ is supplied to the computation section 30 as the detection signal V1. Also, the connection point P− between the second bridge fixed resistor 212 and the variable resistor section 213 is connected to the inverting input terminal of the operational amplifier 221 through a second fixed resistor 223.

Notably, the potential at the connection point P+ between the first bridge fixed resistor 211 and the heat generation resistor 15 and the potential at the connection point P− between the second bridge fixed resistor 212 and the variable resistor section 213 are controlled by feedback control performed by an amplification circuit 220 and a current adjustment circuit 230 in such a manner that the two potentials become the same. Therefore, when the potential at the connection point P− is necessary, the potential at the connection point P+ may be detected instead of the potential at the connection point P−.

Figure 3:
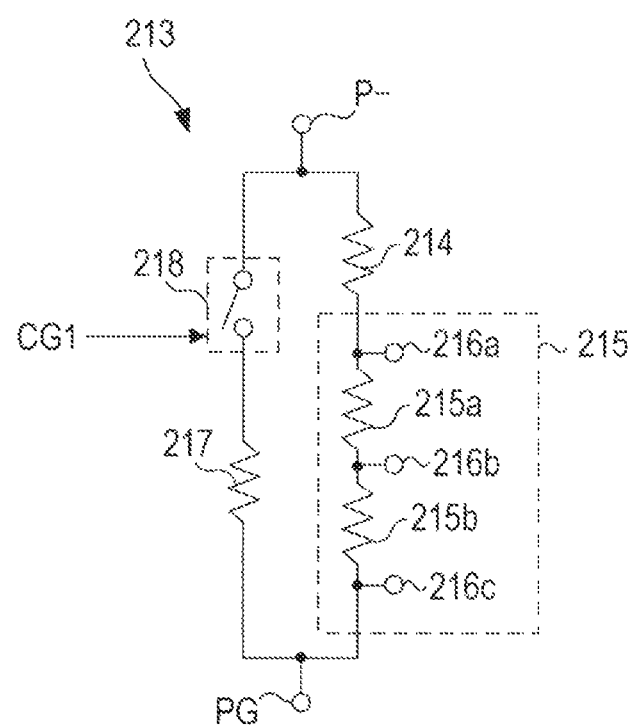
FIG. 3 Circuit diagram showing the circuit configuration of a variable resistor section.

The variable resistor section 213 is configured such that the resistance of the variable resistor section 213 can be switched and is provided so as to change the balance of the bridge circuit 210. FIG. 3 is a circuit diagram showing the circuit configuration of the variable resistor section 213.

The variable resistor section 213 includes a resistor element 214, an adjustment resistor section 215, a resistor element 217, and a changeover switch 218.

The resistor element 214 and the adjustment resistor section 215 are connected in series, one end of the resistor element 214 is connected to the connection point P−, and one end of the adjustment resistor section 215 is connected to the end portion PG. The resistor element 217 and the changeover switch 218 are connected in series, one end of the resistor element 217 is connected to the end portion PG, and one end of the changeover switch 218 is connected to the connection point P−.

The changeover switch 218 performs switching operation in accordance with a changeover signal CG1 output from the computation section 30. Namely, the changeover switch 218 is provided so as to switch the resistance of the variable resistor section 213 between a "resistance corresponding to that of the series circuit of the resistor element 214 and the adjustment resistor section 215" or a "resistance corresponding to that of a circuit formed by connecting the resistor element 217 in parallel to the series circuit of the resistor element 214 and the adjustment resistor section 215."

Notably, the adjustment resistor section 215 includes a resistor element 215a and a resistor element 215b connected in series and has a first terminal 216a, a second terminal 216b, and a third terminal 216c.

The first terminal 216a is connected to an end portion of the resistor element 215a which end portion is connected to the resistor element 214, the second terminal 216b is connected to the connection point between the resistor element 215a and the resistor element 215b, and the third terminal 216c is connected to an end portion of the resistor element 215b which end portion is connected to the end portion PG.

This adjustment resistor section 215 can change the resistance of the adjustment resistor section 215 in accordance with the combination of shorted states of the first terminal 216a, the second terminal 216b, and the third terminal 216c. For example, in a state in which none of the first terminal 216a, the second terminal 216b, and the third terminal 216c is shorted, the resistance of the adjustment resistor section 215 becomes equal to the resistance of the series circuit of the resistor element 215a and the resistor element 215b. Also, in a state in which a short circuit is formed between the first terminal 216a and the second terminal 216b, the resistance of the adjustment resistor section 215 becomes equal to the resistance of the resistor element 215b. Further, in a state in which a short circuit is formed between the second terminal 216b and the third terminal 216c, the resistance of the adjustment resistor section 215 becomes equal to the resistance of the resistor element 215a. Also, in a state in which a short circuit is formed between the first terminal 216a and the third terminal 216c, the resistance of the adjustment resistor section 215 becomes zero.

Notably, the shorted state of the first terminal 216a, the second terminal 216b, and the third terminal 216c is determined at the design stage such that the resistance of the adjustment resistor section 215 becomes equal to a designed target value. At the stage of manufacture of the combustible gas detection apparatus 1, the adjustment resistor section 215 is manufactured such that the shorted state determined at the design stage is realized. Notably, the designed target value for the resistance of the adjustment resistor section 215 is determined in accordance with the use, purpose, etc. of gas detection.

Since the adjustment resistor section 215 having the above-described configuration is provided, the resistance of the variable resistor section 213 can be readily adjusted.

The bridge circuit 210 shown in FIG. 1 is configured to switch the set temperature of the heat generation resistor 15 between a first set temperature CH (a high-temperature-side set temperature; for example, 400° C.) or a second set temperature CL (a low-temperature-side set temperature; for example, 300° C.) by switching the resistance of the variable resistor section 213.

Notably, when the set temperature of the heat generation resistor 15 is set to the first set temperature CH, the changeover switch 218 is turned off (open state), and the resistance of the variable resistor section 213 is set to the "resistance corresponding to that of the series circuit of the resistor element 214 and the adjustment resistor section 215." The voltage between the opposite ends of the heat generation resistor 15 at that time is a high-temperature-time voltage VH.

When the set temperature of the heat generation resistor 15 is set to the second set temperature CL, the changeover switch 218 is turned on (closed state), and the resistance of the variable resistor section 213 is set to the "resistance corresponding to that of the circuit formed by connecting the resistor element 217 in parallel to the series circuit of the resistor element 214 and the adjustment resistor section 215." The voltage between the opposite ends of the heat generation resistor 15 at that time is a low-temperature-time voltage VL.

Notably, in the present embodiment, since the temperature difference between the first set temperature CH (the high-temperature-side set temperature) and the second set temperature CL (the low-temperature-side set temperature) is 100° C. or more, the resolution in the ratio between the high-temperature-time voltage VH and the low-temperature-time voltage VL can be increased. Namely, by accurately calculating the humidity H of the to-be-detected atmosphere by setting the temperature difference between the first set temperature CH and the second set temperature CL to 50° C. or more, the resolution in the ratio between the high-temperature-time voltage VH and the low-temperature-time voltage VL can be increased.

Referring back to FIG. 1, the amplification circuit 220 is a differential amplification circuit and includes the operational amplifier 221, the first fixed resistor 222, the second fixed resistor 223, a third fixed resistor 224, and a capacitor 225. The first fixed resistor 222 is connected between the non-inverting input terminal of the operational amplifier 221 and the connection point P+. The second fixed resistor 223 is connected between the inverting input terminal of the operational amplifier 221 and the connection point P−. The third fixed resistor 224 and the capacitor 225 are connected in parallel between the inverting input terminal of the operational amplifier 221 and the output terminal thereof.

The amplification circuit 220 operates as follows. In the case where the voltage input to the non-inverting input terminal is larger than that input to the inverting input terminal, the value of an adjustment signal C which is an output of the circuit becomes large. As a result, the current flowing to the bridge circuit 210 decreases. In contrast, in the case where the voltage input to the non-inverting input terminal is smaller than that input to the inverting input terminal, the value of the adjustment signal C becomes small. As a result, the current flowing to the bridge circuit 210 increases.

A switching circuit 232 of the current adjustment circuit 230 is connected between a power supply line for supplying a DC power supply voltage Vcc to the bridge circuit 210 and a control line CL1 for changing the energization state of the current adjustment circuit 230. The switching circuit 232 is composed of a transistor which turns on and off in accordance with an operation permission signal S1 from the computation section 30. The switching circuit 232 is configured to output a start signal S11 to the control line CL1 during a period during which the transistor is on. Notably, the predetermined period during which the transistor is turned on is set in advance not to prevent the output of the adjustment signal C.

The constant temperature control circuit 231 of the current adjustment circuit 230 is connected between the power supply line for supplying a DC power supply voltage Vcc and the bridge circuit 210 (specifically, the connection end portion PV). The constant temperature control circuit 231 is composed of a transistor whose conduction state (on resistance) changes in accordance with the signal flowing through the control line CL1. Specifically, the constant temperature control circuit 231 starts the supply of current to the bridge circuit 210 in accordance with the start signal S11 which is the output of the switching circuit 232. After the supply of current to the bridge circuit 210 is started, the on resistance of the transistor changes in accordance with the adjustment signal C. Specifically, when the magnitude of the adjustment signal C increases, the on resistance increases and the current flowing to the bridge circuit 210 decreases. In contrast, when the magnitude of the adjustment signal C decreases, the on resistance decreases and the current flowing to the bridge circuit 210 increases.

In the energization control circuit 21 having the above-described configuration, when the supply of electricity from the DC power supply 40 to the bridge circuit 210 is started, the amplification circuit 220 and the current adjustment circuit 230 perform feedback control for adjusting the current flowing to the bridge circuit 210 such that the potential difference produced between the connection point P+ and the connection point P− becomes zero. As a result, the resistance of the heat generation resistor 15; in other words, the temperature of the heat generation resistor 15, is controlled to a certain value determined by the variable resistor section 213; in other words, the first set temperature CH or the second set temperature CL.

Specifically, in the case where the quantity of heat taken from the heat generation resistor 15 by the combustible gas becomes larger than the quantity of heat generated by the heat generation resistor 15 due to a change in the concentration of the combustible gas contained in the to-be-detected atmosphere, the temperature of the heat generation resistor 15 decreases and the resistance of the heat generation resistor 15 decreases. In contrast, in the case where the quantity of heat taken from the heat generation resistor 15 by the combustible gas becomes smaller than the quantity of heat generated by the heat generation resistor 15, the temperature of the heat generation resistor 15 increases and the resistance of the heat generation resistor 15 increases.

When the resistance of the heat generation resistor 15 decreases as described above, the amplification circuit 220 and the current adjustment circuit 230 increase the current flowing to the bridge circuit 210; in other words, the quantity of heat generated by the heat generation resistor 15. In contrast, when the resistance of the heat generation resistor 15 increases, the amplification circuit 220 and the current adjustment circuit 230 decrease the current flowing to the bridge circuit 210; in other words, the quantity heat generated by the heat generation resistor 15. In this manner, the amplification circuit 220 and the current adjustment circuit 230 perform feedback control such that the resistance of the heat generation resistor 15; in other words, the temperature of the heat generation resistor 15, approaches a predetermined value.

By measuring the detection signal V1 representing the potential at the connection point P+, the quantity of heat necessary to maintain constant the magnitude of the current flowing to the heat generation resistor 15; i.e., the temperature (in other words, the resistance) of the heat generation resistor 15 is found. The quantity of heat taken from the heat generation resistor 15 by the combustible gas (hydrogen gas) is found, and the quantity of the taken heat depends on the concentration of the hydrogen gas. Therefore, the concentration of the hydrogen gas can be determined by measuring the detection signal V1.

1-3. Temperature Adjustment Circuit

Next, the temperature adjustment circuit 25 will be described. The temperature adjustment circuit 25 includes a bridge circuit 250 which is a Wheatstone bridge circuit including the temperature measurement resistor 16, and an amplification circuit 260 which amplifiers a potential difference obtained from the bridge circuit 250.

The bridge circuit 250 is a Wheatstone bridge circuit including the temperature measurement resistor 16, a first bridge fixed resistor 251, a second bridge fixed resistor 252, and a third bridge fixed resistor 253.

The first bridge fixed resistor 251 is connected in series to the temperature measurement resistor 16. Of end portions of the temperature measurement resistor 16, the end portion opposite the end portion connected to the first bridge fixed resistor 251 is grounded. Of end portions of the first bridge fixed resistor 251, the end portion connected to the second bridge fixed resistor 252 is connected to the power supply line for supplying the DC power supply voltage Vcc.

Also, the second bridge fixed resistor 252 is connected in series to the third bridge fixed resistor 253. Of the end portions of the third bridge fixed resistor 253, end portion opposite the end portion connected to the second bridge fixed resistor 252 is grounded. Of end portions of the second bridge fixed resistor 252, the end portion connected to the first bridge fixed resistor 251 is connected to the power supply line for supplying the DC power supply voltage Vcc.

The connection point P− between the first bridge fixed resistor 251 and the temperature measurement resistor 16 is connected to the inverting input terminal of an operational amplifier 261 through a second temperature adjustment resistor 263. The connection point P+ between the second bridge fixed resistor 252 and the third bridge fixed resistor 253 is connected to the non-inverting input terminal of the operational amplifier 261 through a first temperature adjustment fixed resistor 262. Also, the output of the operational amplifier 261 is supplied to the computation section 30 as a temperature detection signal VT.

The amplification circuit 260 is a differential amplification circuit and includes the operational amplifier 261, the first temperature adjustment fixed resistor 262, the second temperature adjustment resistor 263, a third fixed resistor 264, and a capacitor 265. The first temperature adjustment fixed resistor 262 is connected between the non-inverting input terminal of the operational amplifier 261 and the connection point P+. The second temperature adjustment resistor 263 is connected between the inverting input terminal of the operational amplifier 261 and the connection point P−. The third fixed resistor 264 and the capacitor 265 are connected in parallel between the inverting input terminal of the operational amplifier 261 and the output terminal thereof.

1-4. Computation Section

The computation section 30 computes the concentration of hydrogen gas on the basis of the temperature detection signal VT output from the temperature adjustment circuit 25 and the detection signal V1 output from the energization control circuit 21. The computation section 30 starts upon supply of electricity from the DC power supply 40. After the startup, the computation section 30 initializes various sections and starts gas concentration computation processing.

The computation section 30 includes a central processing unit (CPU) for executing various types of computation processing such as the gas concentration computation processing; a storage device such as ROM and RAM which stores various programs, data, etc. for causing the CPU to execute various types of computation processing; an IO port for inputting and outputting various types of signals; a timer for clocking; etc. (not illustrated).

The above-described storage device stores at least temperature conversion data, voltage conversion data, humidity conversion data, and concentration conversion data. Also, the storage device stores a computation formula or the like for computing a reference resistance R0 on the basis of a reference top potential V20 and a reference intermediate potential V10, which will be described later.

The temperature conversion data includes temperature conversion data which represents the correlation between the reference resistance R0 and a reference judgment temperature T0 of the heat generation resistor 15; temperature conversion data which represents the correlation between a detection-time resistance R1 and a detection-time judgment temperature T1 of the heat generation resistor 15; and temperature conversion data which represents the correlation between the environmental temperature T of the to-be-detected atmosphere and the temperature voltage VT (the temperature detection signal VT).

The voltage conversion data includes voltage conversion data which represents the correlation between the temperature of the heat generation resistor 15 and the voltage between the opposite ends of the heat generation resistor 15.

The humidity conversion data includes humidity conversion data which represents the correlation between the humidity H within the to-be-detected atmosphere and the high-temperature-time voltage VH, the low-temperature-time voltage VL, and the temperature voltage.

The concentration conversion data includes concentration conversion data which represents the correlation between the high-temperature-time voltage VH or the low-temperature-time voltage VL and the gas concentration X of the combustible gas.

Notably, the present embodiment is configured to use concentration conversion data which represents the correlation between the high-temperature-time voltage VH and the gas concentration X of hydrogen gas. Notably, each conversion data is composed of map data for conversion, a calculation formula for conversion, or the like, and is prepared in advance on the basis of data obtained through an experiment or the like.

The above-mentioned humidity conversion data includes map data for voltage ratio conversion which represents the correlation between the environmental temperature T (the temperature voltage VT) and voltage ratio VC(0) to be described later; and map data for humidity conversion which represents the correlation between voltage ratio difference $\Delta VC$ to be described later and the humidity H.

The above-mentioned concentration conversion data includes map data for high-temperature-time voltage conversion which represents the correlation between the temperature voltage VT and high-temperature-time voltage VH(0) to be described later; map data for humidity voltage change conversion which represents the correlation between the high-temperature-time voltage VH and the humidity H, and high-temperature-time voltage change $\Delta VH(H)$ to be described later; and map data for gas sensitivity conversion which represents the correlation between the temperature voltage VT and the high-temperature-time voltage VH, and gas sensitivity G(VT) to be described later.

1-5. Method of Detecting Concentration of Hydrogen Gas

Figure 4A:
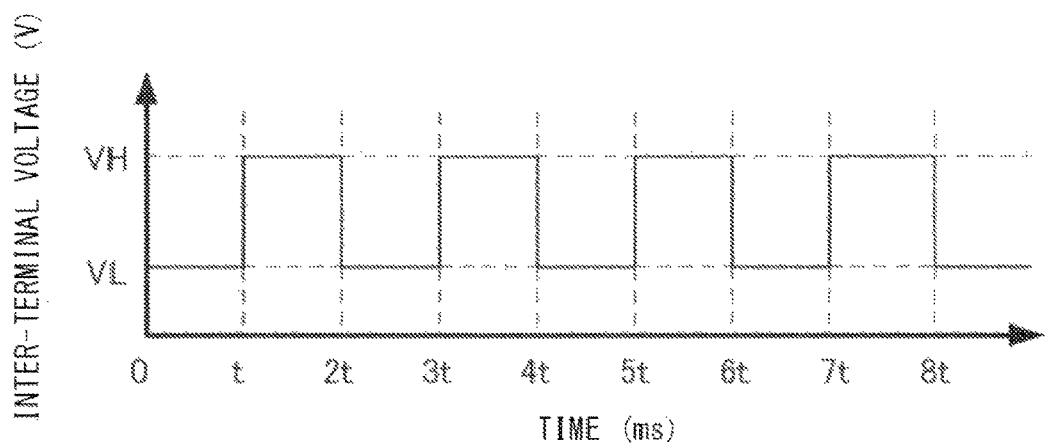
FIG. 4A Graph describing a change in the inter-terminal voltage of a heat generation resistor with time.
Figure 4B:
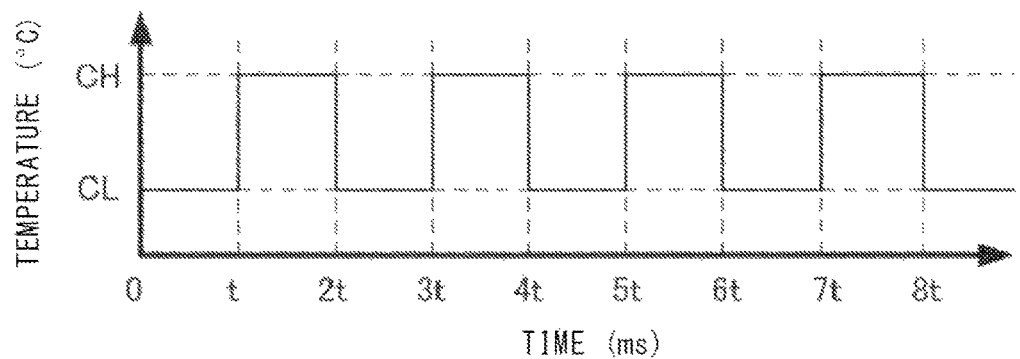
FIG. 4B Graph describing a change in the temperature of the heat generation resistor with time.

Next, the method of detecting the concentration of hydrogen gas performed by the combustible gas detection apparatus 1 of the present embodiment will be described. When the concentration of hydrogen gas is to be detected, as shown in FIGS. 4(*a*) and 4(*b*), the combustible gas detection apparatus 1 alternately and repeatedly performs control processing of holding the set temperature of the heat generation resistor 15 at the low-temperature-side second set temperature CL during a predetermined periodic time t (hereinafter referred to as the "low temperature period t") and control processing of holding the set temperature of the heat generation resistor 15 at the high-temperature-side first set temperature CH during a predetermined periodic time t (hereinafter referred to as the "high temperature period t").

Specifically, the computation section 30 of the combustible gas detection apparatus 1 outputs the changeover signal CG1 so as to alternately and repeatedly performs control processing of holding the resistance of the bridge circuit 210; i.e., the inter-terminal voltage of the heat generation resistor 15, at the low-temperature-time voltage VL during the low temperature period t and control processing of holding the inter-terminal voltage of the heat generation resistor 15 at the high-temperature-time voltage VH during the high temperature period t.

In the present embodiment, the low temperature period t and the high temperature period t have the same length; specifically, 200 ms. Notably, the total length of one cycle (2t) including the low temperature period t and the high temperature period t is preferably 5 seconds or less. This is because when the length of one cycle increases, the followability of the output to an environmental change; in other words, the accuracy of the output, deteriorates.

The computation section 30 executes various types of control processing such as reference judgment value computation processing to be executed before shipment of the combustible gas detection apparatus 1 and gas concentration computation processing to be executed at the time of gas detection.

First, the reference judgment value computation processing will be described.

Figure 5:
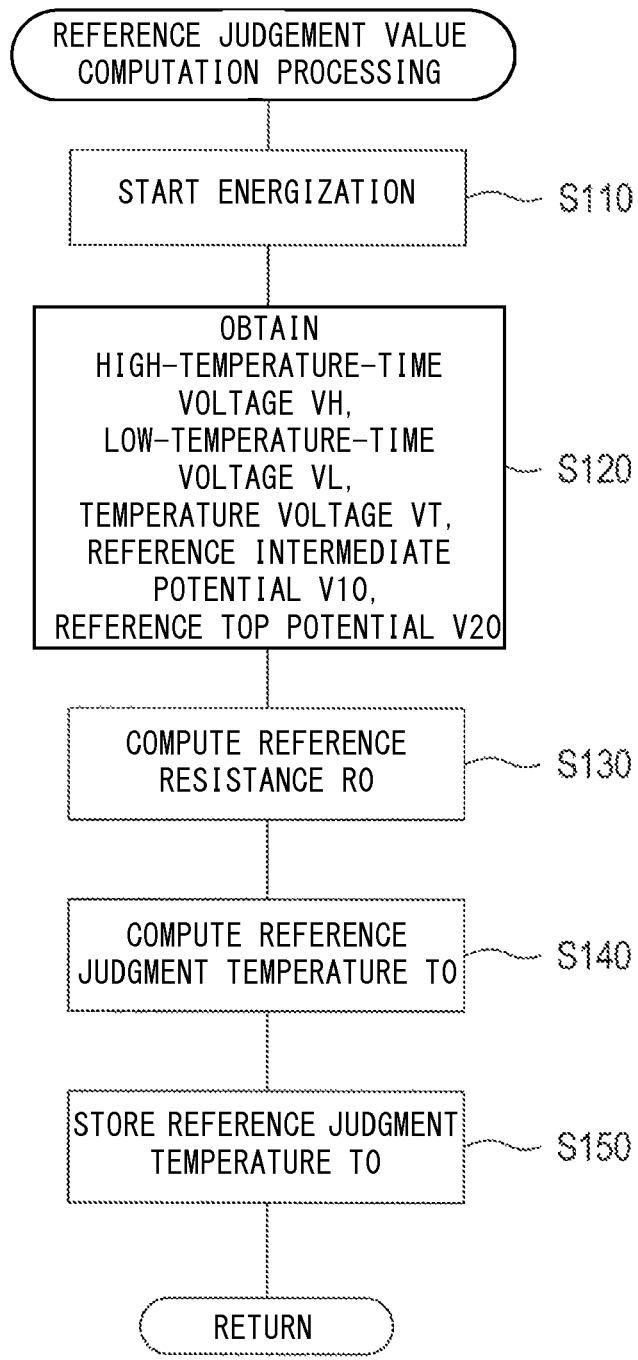
FIG. 5 Flowchart showing the details of reference judgment value computation processing.

The reference judgment value computation processing is control processing which is executed only one time before shipment of the combustible gas detection apparatus 1 so as to calculate the reference judgment temperature T0. FIG. 5 is a flowchart showing the details of the reference judgment value computation processing.

When the reference judgment value computation processing is started, in S110 (S stands for step), the computation section 30 first starts the supply of electricity to various sections within the apparatus. Specifically, the computation section 30 starts the supply of electricity to the heat generation resistor 15 by the energization control circuit 21 and the supply of electricity to the temperature measurement resistor 16 by the temperature adjustment circuit 25.

In the next step S120, the computation section 30 obtains the low-temperature-time voltage VL, the high-temperature-time voltage VH, the reference top potential V20, and the reference intermediate potential V10 from the energization control circuit 21 and obtains the temperature voltage VT from the temperature adjustment circuit 25.

Notably, the reference top potential V20 is the potential of the TOP voltage signal V2 detected at that time; the reference intermediate potential V10 is the potential of the detection signal V1 detected at that time; and the temperature voltage VT is the voltage of the temperature detection signal VT detected at that time.

In the next step S130, the computation section 30 computes the reference resistance R0 on the basis of [Formula 1].

$$R0 = R211 \times \frac{V10}{(V20 - V10)} \quad \text{[Formula 1]}$$

Notably, R211 is the resistance of the first bridge fixed resistor 211.

In the next step S140, the computation section 30 computes the reference judgment temperature T0 using the reference resistance R0 obtained in S130. Notably, in the present embodiment, the computation section 30 computes the reference judgment temperature T0 through use of the temperature conversion data (temperature conversion data representing the correlation between the reference resistance R0 and the reference judgment temperature T0 of the heat generation resistor 15) stored in the storage device.

Notably, the value of the reference resistance R0 is determined by the resistances of the second bridge fixed resistor 212 and the variable resistor section 213 before shipment of the combustible gas detection apparatus 1. Also, the value of the reference judgment temperature T0 computed on the basis of the reference resistance R0 is also determined by the resistances of the second bridge fixed resistor 212 and the variable resistor section 213 before shipment of the combustible gas detection apparatus 1.

In the next step S150, the computation section 30 stores the reference judgment temperature T0 obtained in S140 in the storage device.

When the processing in S150 is completed, the reference judgment value computation processing ends.

In the above-described manner, the reference judgment value computation processing computes the reference judgment temperature T0 and stores the reference judgment temperature T0 in the storage device.

Next, the gas concentration computation processing will be described.

Figure 6:
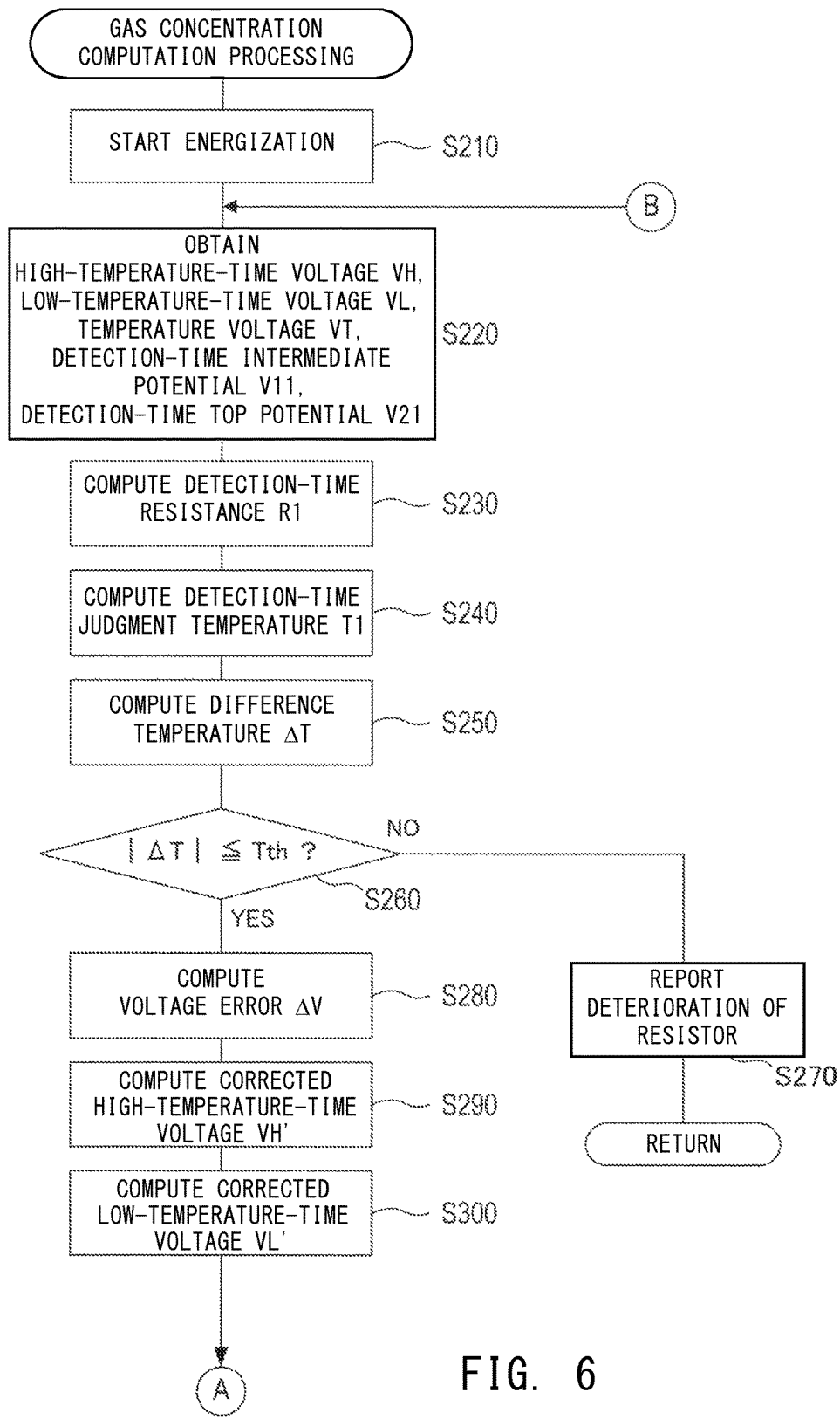
FIG. 6 Flowchart showing the details of a first half of gas concentration computation processing.
Figure 7:
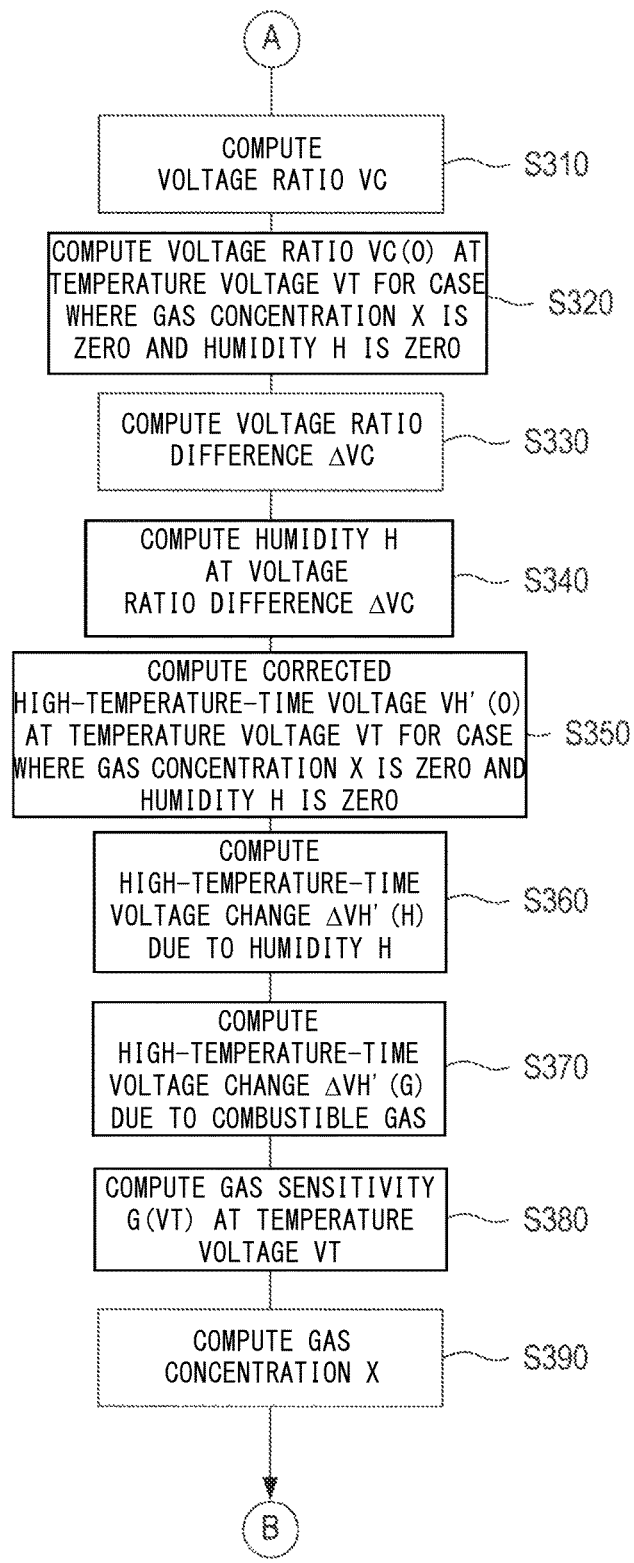
FIG. 7 Flowchart showing the details of a second half of the gas concentration computation processing.

The gas concentration computation processing is control processing which is executed at the time of gas detection by the combustible gas detection apparatus 1 so as to compute the concentration of the combustible gas. Notably, execution of the gas concentration computation processing is permitted in a state in which the reference judgment temperature T0 is stored in the storage device as a result of execution of the reference judgment value computation processing. FIG. 6 is a flowchart showing the details of a first half of the gas concentration computation processing, and FIG. 7 is a flowchart showing the details of a second half of the gas concentration computation processing.

When the gas concentration computation processing is started, in S210, the computation section 30 first starts the supply of electricity to various sections within the apparatus. Specifically, the computation section 30 starts the supply of electricity to the heat generation resistor 15 by the energization control circuit 21 and the supply of electricity to the temperature measurement resistor 16 by the temperature adjustment circuit 25.

In the next step S220, the computation section 30 obtains the low-temperature-time voltage VL, the high-temperature-time voltage VH, a detection-time top potential V21, and a detection-time intermediate potential V11 from the energization control circuit 21 and obtains the temperature voltage VT from the temperature adjustment circuit 25.

Notably, the detection-time top potential V21 is the potential of the TOP voltage signal V2 detected at that time; the detection-time intermediate potential V11 is the potential of the detection signal V1 detected at that time; and the temperature voltage VT is the voltage of the temperature detection signal VT detected at that time.

In the next step S230, the computation section 30 computes the detection-time resistance R1 on the basis of [Formula 2].

$$R1 = R211 \times \frac{V11}{(V21 - V11)} \quad \text{[Formula 2]}$$

Notably, R211 is the resistance of the first bridge fixed resistor 211.

In the next step S240, the computation section 30 computes the detection-time judgment temperature T1 using the detection-time resistance R1 obtained in S230. Notably, in the present embodiment, the computation section 30 computes the detection-time judgment temperature T1 through use of the temperature conversion data (temperature conversion data representing the correlation between the detection-time resistance R1 and the detection-time judgment temperature T1 of the heat generation resistor 15) stored in the storage device.

Notably, the value of the detection-time resistance R1 is determined by the resistances of the second bridge fixed resistor 212 and the variable resistor section 213 at the time of gas detection by the combustible gas detection apparatus 1. Also, the value of the detection-time judgment temperature T1 computed on the basis of detection-time resistance R1 is also determined by the resistances of the second bridge fixed resistor 212 and the variable resistor section 213 at the time of gas detection by the combustible gas detection apparatus 1.

In the next step S250, the computation section 30 computes the difference (difference temperature ΔT) between the detection-time judgment temperature T1 obtained in S240 and the reference judgment temperature T0 stored in the storage device.

$$\Delta T = T1 - T0 \qquad \text{[Formula 3]}$$

The reference judgment temperature T0 assumes a value corresponding to each resistance of the second bridge fixed resistor 212 and the variable resistor section 213 before shipment of the combustible gas detection apparatus 1, and the detection-time judgment temperature T1 assumes a value corresponding to each resistance of the second bridge fixed resistor 212 and the variable resistor section 213 at the time of gas detection by the combustible gas detection apparatus 1.

Therefore, the difference temperature ΔT assumes a value corresponding to the difference between the resistance of the second bridge fixed resistor 212 (or the variable resistor section 213) before shipment of the combustible gas detection apparatus 1 and that at the time of gas detection by the combustible gas detection apparatus 1. In other words, the difference temperature ΔT assumes a value corresponding to the difference between the deteriorated state of the second bridge fixed resistor 212 (or the variable resistor section 213) before shipment of the combustible gas detection apparatus 1 and that at the time of gas detection by the combustible gas detection apparatus 1.

In the next step S260, the computation section 30 judges whether or not the absolute value of the difference temperature ΔT is equal to or smaller than a judgment threshold Tth. In the case where the result of the judgement is "Yes," the computation section 30 proceeds to S280. In the case where the result of the judgement is "No," the computation section 30 proceeds to S270.

Notably, as the judgment threshold Tth, there is set a boundary value between a numerical range within which the absolute value of the difference temperature ΔT falls when at least one of the second bridge fixed resistor 212 and the variable resistor section 213 is in a deteriorated state and a numerical range within which the absolute value of the difference temperature ΔT falls when none of the second bridge fixed resistor 212 and the variable resistor section 213 are in a deteriorated state. In the present embodiment, "1.0" is set as the judgment threshold Tth.

In the case where the result of the judgement in S260 is "Yes," the computation section 30 can determine that none of the second bridge fixed resistor 212 and the variable resistor section 213 of the bridge circuit 210 have not deteriorated. In the case where the result of the judgement in S260 is "No," the computation section 30 can determine that one of the second bridge fixed resistor 212 and the variable resistor section 213 of the bridge circuit 210 has deteriorated.

Therefore, in the case where the result of the judgement in S260 is "No" and the computation section 30 proceeds to S270, in S270, the computation section 30 performs processing of reporting that a resistor has deteriorated. For example, the computation section 30 notifies a user of the deterioration of the resistor by displaying the deteriorated state of the resistor on a display section (not shown) provided on the combustible gas detection apparatus 1.

When the processing in S270 is completed, the gas concentration computation processing ends.

Meanwhile, in the case where the result of the judgement in S260 is "Yes" and the computation section 30 proceeds to S280, in S280, the computation section 30 computes a voltage error ΔV1 on the basis of the difference temperature ΔT. At that time, the computation section 30 computes the voltage error ΔV1 through use of the voltage conversion data representing the correlation between the temperature of the heat generation resistor 15 and the voltage between the opposite ends of the heat generation resistor 15.

In the next step S290, the computation section 30 corrects the high-temperature-time voltage VH through use of the voltage error ΔV1 obtained in S280 to thereby compute a corrected high-temperature-time voltage VH'. Specifically, the computation section 30 computes the corrected high-temperature-time voltage VH' through use of the following [Formula 4].

$$VH' = VH - \Delta V1 \qquad \text{[Formula 4]}$$

In the next step S300, the computation section 30 computes a corrected low-temperature-time voltage VL' through use of the corrected high-temperature-time voltage VH' obtained in S290 and the ratio between the high-temperature-time voltage VH and the low-temperature-time voltage VL. Specifically, the computation section 30 computes the corrected low-temperature-time voltage VL' through use of the following [Formula 5].

$$VL' = \frac{VL}{VH} \times VH' \qquad \text{[Formula 5]}$$

Notably, the method of computing the corrected low-temperature-time voltage VL' is not limited to the method in which [Formula 5] is used. For example, the corrected low-temperature-time voltage VL' may be computed through use of the voltage error ΔV1 by the same method as the method of computing the corrected high-temperature-time voltage VH' through use of [Formula 4].

In the next step S310, the computation section 30 computes a voltage ratio VC on the basis of the corrected high-temperature-time voltage VH' and the corrected low-temperature-time voltage VL'. Specifically, the computation section 30 computes the voltage ratio VC through use of the following [Formula 6].

$$VC = \frac{VH'}{VL'} \qquad \text{[Formula 6]}$$

In the next step S320, on the basis of the temperature voltage VT obtained in S220 and the map data for voltage ratio conversion, the computation section 30 computes a voltage ratio VC(0) corresponding to the environmental temperature T (the temperature voltage VT) for the case where the gas concentration X is zero and the humidity H is zero.

In the next step S330, the computation section 30 computes a voltage ratio difference ΔVC corresponding to the environmental temperature T (the temperature voltage VT) while using the voltage ratio VC obtained in S310 and the voltage ratio VC(0) obtained in S320 as input values of [Formula 7].

$$\Delta VC = VC - VC(0) \quad \text{[Formula 7]}$$

In the next step S340, the computation section 30 computes the humidity H corresponding to the voltage ratio difference ΔVC on the basis of the voltage ratio difference ΔVC obtained in S330 and the map data for humidity conversion.

In the next step S350, on the basis of the corrected high-temperature-time voltage VH' obtained in S290, the temperature voltage VT obtained in S220, and the map data for high-temperature-time voltage ratio conversion, the computation section 30 computes a corrected high-temperature-time voltage ratio VH'(0) corresponding to the environmental temperature T (the temperature voltage VT) for the case where the gas concentration X is zero and the humidity H is zero.

In the next step S360, on the basis of the corrected high-temperature-time voltage VH' obtained in S290, the humidity H obtained in S340, and the map data for humidity voltage change conversion, the computation section 30 computes a high-temperature-time voltage change ΔVH'(H) which represents a voltage change of the corrected high-temperature-time voltage VH' due to the humidity H.

In the next step S370, the computation section 30 computes a high-temperature-time voltage change ΔVH'(G) which represents a voltage change of the corrected high-temperature-time voltage VH' due to the combustible gas while using the corrected high-temperature-time voltage VH' obtained in S290, the high-temperature-time voltage VH'(0) obtained in S350, and the high-temperature-time voltage change ΔVH'(H) obtained in S360 as input values of [Formula 8].

$$\Delta VH'(G) = VH' - VH'(0) - \Delta VH'(H) \quad \text{[Formula 8]}$$

In the next step S380, the computation section 30 computes a gas sensitivity G(VT) which represents the sensitivity to the combustible gas after correction (the unit is the reciprocal of the gas concentration X) on the basis of the corrected high-temperature-time voltage VH' obtained in S290, the temperature voltage VT obtained in S220, and the map data for gas sensitivity conversion.

In the next step S390, the computation section 30 computes the gas concentration X of the combustible gas (hydrogen) while using the high-temperature-time voltage change ΔVH'(G) calculated in S370 and the gas sensitivity G(VT) calculated in S380 as input values of [Formula 9].

$$X = \frac{\Delta VH'(G)}{G(VT)} \quad \text{[Formula 9]}$$

After completion of S390, the computation section 30 again proceeds to S220 and repeatedly executes the above-described processing.

As described above, in the gas concentration computation processing, the deteriorated state of the second bridge fixed resistor 212 and the variable resistor section 213 of the bridge circuit 210 can be judged on the basis of the absolute value of the difference temperature ΔT.

Also, in the gas concentration computation processing, the high-temperature-time voltage VH and the low-temperature-time voltage VL are corrected through use of the difference temperature ΔT, and the gas concentration X is computed through use of the corrected high-temperature-time voltage VH' and the corrected low-temperature-time voltage VL' obtained through the correction. In other words, in the gas concentration computation processing, the gas concentration X is computed by correcting the voltage between the opposite ends of the heat generation resistor 15 (the high-temperature-time voltage VH and the low-temperature-time voltage VL) through use of the difference temperature ΔT.

1-6. Effects

As described above, in the combustible gas detection apparatus 1 of the present embodiment, the first bridge fixed resistor 211 is composed of a resistor element which is less likely to deteriorate as compared with the second bridge fixed resistor 212 and the variable resistor section 213 (in other words, a resistor element having a characteristic that it is small in the ratio of a change in resistance due to deterioration with elapse of time or deterioration caused by environmental load (deterioration caused by the influence of temperature, humidity, energization, etc.)).

Therefore, when the second bridge fixed resistor 212 and the variable resistor section 213 are compared with the first bridge fixed resistor 211, the second bridge fixed resistor 212 and the variable resistor section 213 become more likely to deteriorate earlier than does the first bridge fixed resistor 211.

The reference judgment temperature T0 assumes a value corresponding to the resistances of the second bridge fixed resistor 212 and the variable resistor section 213 before shipment of the combustible gas detection apparatus 1, and the detection-time judgment temperature T1 assumes a value corresponding to the resistances of the second bridge fixed resistor 212 and the variable resistor section 213 at the time of gas detection by the combustible gas detection apparatus 1.

In the case where both the second bridge fixed resistor 212 and the variable resistor section 213 remain undeteriorated at the time of gas detection, the resistances of the second bridge fixed resistor 212 and the variable resistor section 213 at the time of gas detection do not differ greatly from those before shipment of the combustible gas detection apparatus 1. Therefore, in the case where both the second bridge fixed resistor 212 and the variable resistor section 213 remain undeteriorated at the time of gas detection, the detection-time judgment temperature T1 assumes a value approximately the same as the reference judgment temperature T0, and the absolute value of the difference temperature ΔT which is the difference between the detection-time judgment temperature T1 and the reference judgment temperature T0 is small.

Meanwhile, in the case where at least one of the second bridge fixed resistor 212 and the variable resistor section 213 is in a deteriorated state at the time of gas detection, the resistance of at least one of the second bridge fixed resistor 212 and the variable resistor section 213 at the time of gas detection changes to a value corresponding to the deteriorated state. Therefore, in the case where at least one of the second bridge fixed resistor 212 and the variable resistor section 213 is in a deteriorated state at the time of gas detection, the detection-time judgment temperature T1 assumes a value different from the reference judgment temperature T0, and the absolute value of the difference temperature ΔT which is the difference between the detection-time judgment temperature T1 and the reference judgment temperature T0 become large. In particular, the greater the degree of deterioration, the greater the absolute value of the difference temperature ΔT which is the difference between the detection-time judgment temperature T1 and the reference judgment temperature T0.

Because of these, as a result of execution of S260 of the gas concentration detection processing, the computation section 30 can judge the deteriorated state of at least one of the second bridge fixed resistor 212 and the variable resistor section 213 on the basis of the absolute value of the difference between the detection-time judgment temperature T1 and the reference judgment temperature T0 (the difference temperature ΔT).

Therefore, in the combustible gas detection apparatus 1, deterioration of the second bridge fixed resistor 212 and the variable resistor section 213 provided in the bridge circuit 210 can be detected.

In the case where none of the second bridge fixed resistor 212 and the variable resistor section 213 are in a deteriorated state at the time of gas detection, the detection signal V1 corresponding to the voltage between the opposite ends of the heat generation resistor 15 assumes a proper value corresponding to the hydrogen concentration (the concentration of the specific gas).

Meanwhile, in the case where at least one of the second bridge fixed resistor 212 and the variable resistor section 213 is in a deteriorated state at the time of gas detection, since the detection signal V1 corresponding to the voltage between the opposite ends of the heat generation resistor 15 changes as a result of the influence of the deteriorated state of the second bridge fixed resistor 212 (or the variable resistor section 213), the detection signal V1 assumes a value different from the proper value corresponding to the hydrogen concentration (the concentration of the specific gas).

The amount of the change in the voltage between the opposite ends of the heat generation resistor 15 changes in accordance with the deteriorated state of the second bridge fixed resistor 212 (or the variable resistor section 213). Therefore, through execution of S290 of the gas concentration detection processing, the computation section 30 corrects the high-temperature-time voltage VH through use of the voltage error ΔV1 to thereby compute the corrected high-temperature-time voltage VH'. This corrected high-temperature-time voltage VH' corresponds to the corrected voltage between the opposite ends of the heat generation resistor 15 which is corrected so as to mitigate the influence of the deteriorated state of the second bridge fixed resistor 212 (or the variable resistor section 213).

Similarly, the corrected low-temperature-time voltage VL' corresponds to the corrected voltage between the opposite ends of the heat generation resistor 15 which is corrected so as to mitigate the influence of the deteriorated state of the second bridge fixed resistor 212 (or the variable resistor section 213).

As a result, when the computation section 30 computes the hydrogen concentration (the concentration of the specific gas) through use of the voltage between the opposite ends of the heat generation resistor 15 (the detection signal V1) by executing the gas concentration detection processing, the computation section 30 can compute the hydrogen concentration (the concentration of the specific gas) while mitigating the influence of the deteriorated state of the second bridge fixed resistor 212 (or the variable resistor section 213).

Therefore, in the combustible gas detection apparatus 1, even in the case where at least one of the second bridge fixed resistor 212 and the variable resistor section 213 provided in the bridge circuit 210 deteriorates and its resistance changes, a decrease in the accuracy in detecting the hydrogen concentration can be suppressed.

The combustible gas detection apparatus 1 includes the temperature measurement resistor 16 whose resistance changes as a result of a change in the environmental temperature which is the temperature of the to-be-detected atmosphere, and the computation section 30 which executes the gas concentration detection processing obtains the environmental temperature T (thus, the temperature voltage VT) detected on the basis of the resistance of the temperature measurement resistor 16.

The computation section 30 which executes the gas concentration detection processing computes the hydrogen concentration (the concentration of the specific gas) through use of the temperature voltage VT which changes in accordance with the resistance of the temperature measurement resistor 16 in addition to the detection signal V1 corresponding to the voltage between the opposite ends of the heat generation resistor 15.

Since the hydrogen concentration (the concentration of the specific gas) is computed through use of the environmental temperature T in addition to the voltage between the opposite ends of the heat generation resistor 15 as described above, it is possible to compute the hydrogen concentration (the concentration of the specific gas) while suppressing the influence of a change in the environmental temperature T.

Therefore, according to the combustible gas detection apparatus 1, it is possible to compute the hydrogen concentration (the concentration of the specific gas) while suppressing the influence of a change in the environmental temperature T. Thus, the accuracy in detecting the hydrogen concentration (the concentration of the specific gas) can be improved.

In the combustible gas detection apparatus 1, the detection signal V1 not only serves as the detection signal corresponding to the voltage between the opposite ends (inter-terminal voltage) of the heat generation resistor 15 but also serves as the first intermediate potential signal V3 corresponding to the potential at the connection point P+ between the first bridge fixed resistor 211 and the heat generation resistor 15 and the second intermediate potential signal V4 corresponding to the potential at the connection point P− between the second bridge fixed resistor 212 and the variable resistor section 213.

Therefore, even though the combustible gas detection apparatus 1 has a simple configuration including only a signal path for detecting the potential at the connection point P+ rather than a complex configuration including signal paths for individually detecting the voltage between the opposite ends (inter-terminal voltage) of the heat generation resistor 15, the potential at the connection point P+, and the potential at the connection point P−, its detection value can be utilized as the voltage between the opposite ends (inter-terminal voltage) of the heat generation resistor 15 and the potential at the connection point P−.

Therefore, according to the combustible gas detection apparatus 1, it is possible to judge whether or not the heat generation resistor 15 has deteriorated and improve the accuracy in detecting the hydrogen concentration (the concentration of the specific gas) while employing a simple configuration for the signal path.

1-7. Correspondence Between Embodiment and Claims

A description will be given of the correspondence between terms used in claims and terms used in the present embodiment.

The combustible gas detection apparatus 1 corresponds to an example of the gas detector; the bridge circuit 210 corresponds to an example of the Wheatstone bridge circuit; the amplification circuit 220 and the current adjustment circuit 230 correspond to an example of the bridge control section; and the computation section 30 corresponds to an example of the computation section.

The first bridge fixed resistor 211 corresponds to an example of the first resistor section; the second bridge fixed resistor 212 corresponds to an example of the second resistor section; and the variable resistor section 213 corresponds to an example of the third resistor section.

The end portion PG corresponds to an example of the reference point; the connection end portion PV corresponds to an example of the high potential point; the connection point P+ corresponds to an example of the first potential point; and the connection point P− corresponds to an example of the second potential point.

The computation section 30 which executes the gas concentration computation processing corresponds to an example of the gas concentration computation section; the reference judgment temperature T0 corresponds to an example of the reference judgment value; the computation section 30 which executes S150 corresponds to an example of the reference judgment value computation section; the detection-time judgment temperature T1 corresponds to an example of the detection-time judgment value; the detection-time intermediate potential V11 corresponds to an example of the detection-time potential; the computation section 30 which executes S220 corresponds to an example of the obtainment section; and the computation section 30 which executes S240 corresponds to an example of the detection-time judgment value computation section.

The computation section 30 which executes S260 corresponds to an example of the deterioration judgment section; and the computation section 30 which executes S290 and S300 corresponds to an example of the voltage correction section.

2. Other Embodiments

Although an embodiment of the present invention has been described, the present invention is not limited to the above-described embodiment and can be implemented in various forms without departing from the scope of the invention.

For example, in the above-described embodiment, a signal path for supplying the potential at the connection point P− between the second bridge fixed resistor 212 and the variable resistor section 213 to the computation section 30 is not provided, only a signal path for supplying the potential at the connection point P+ between the first bridge fixed resistor 211 and the heat generation resistor 15 to the computation section 30 is provided, and the potential at the connection point P+ is used as the potential at the connection point P−. However, the configuration of the signal path is not limited to such a configuration. For example, a signal path for supplying the potential at the connection point P− between the second bridge fixed resistor 212 and the variable resistor section 213 to the computation section 30 may be provided so as to allow the computation section 30 to receive the potential at the connection point P− through this signal path.

Also, in the above-described embodiment, the Wheatstone bridge circuit is configured such that one end of the heat generation resistor is connected to the reference point; however, the Wheatstone bridge circuit may be configured such that one end of the heat generation resistor is connected to the high potential point.

Also, the above-described judgment threshold Tth is not limited to "1.0" and an arbitrary value may be set as the judgment threshold Tth so long as the value allows the judgement as to whether or not the resistor section of the Wheatstone bridge circuit has deteriorated.

Also, in the above-described embodiment, the deterioration judgement processing and the voltage correction processing (processing of correcting the high-temperature-time voltage VH and the low-temperature-time voltage VL) are always executed when the gas detector is operating. However, the execution timings of these processing operations is not limited to "always." For example, these processing operations may be performed every time the gas detector is started or at predetermined time intervals.

Also, the deterioration judgement processing and the voltage correction processing may be performed through use of a value obtained by averaging a predetermined number of obtained data sets. The method for averaging may be arithmetic averaging or moving averaging.

Further, since the corrected voltage value is likely to change greatly immediately after the startup of the gas detector, the voltage correction processing may be executed after elapse of a predetermined time (e.g., 5 sec) after the startup.

In the above-described embodiment, the gas detector is configured to perform deterioration judgement and voltage correction through use of the difference (the difference temperature ΔT) between the reference judgment value (the reference judgment temperature T0) and the detection-time judgment value (the detection-time judgment temperature T1). However, the configuration of the gas detector is not limited to such a configuration. For example, the gas detector may be configured to perform deterioration judgement and voltage correction through use of the ratio (the temperature ratio Tr (=T1/T0)) between the reference judgment value (the reference judgment temperature T0) and the detection-time judgment value (the detection-time judgment temperature T1). In this case, when the temperature ratio Tr assumes a value close to 1.0, the gas detector judges that the resistor section has not yet deteriorated, and when the temperature ratio Tr assumes a value deviating far from 1.0, the gas detector judges that the resistor section has deteriorated.

The timing of execution of the reference judgment value computation processing may be any timing before shipment of the gas detector so long as the reference judgment value computation processing is executed before shipment of the gas detector.

In the above-described embodiment, the gas detector is configured such that the reference judgment value (the reference judgment temperature T0) is computed by the reference judgment value computation processing. However, the configuration of the gas detector is not limited to such a configuration, and the gas detector may be configured such that the reference judgment value is stored in the storage section (ROM, etc.) in advance. Also, the storage section is not limited to the ROM, and other types of storage sections such as EEPROM may be used.

DESCRIPTION OF SYMBOLS

1 . . . combustible gas detection apparatus, 10 . . . gas detection element, 15 . . . heat generation resistor, 16 . . . temperature measurement resistor, 20 . . . control section, 21 . . . energization control circuit, 25 . . . temperature adjustment circuit, 30 . . . computation section, 40 . . . DC power supply, 210 . . . bridge circuit, 211 . . . first bridge fixed resistor, 212 . . . second bridge fixed resistor, 213 . . . variable resistor section, 214 . . . resistor element, 215 . . . adjustment resistor section, 215a . . . resistor element, 215b . . . resistor element, 216a . . . first terminal, 216b . . . second terminal, 216c . . . third terminal, 217 . . . resistor element, 218 . . . changeover switch, 220 . . . amplification circuit, 221 . . . operational amplifier, 222 . . . first fixed resistor, 223 . . . second fixed resistor, 224 . . . third fixed resistor, 230 . . . current adjustment circuit, 231 . . . constant temperature control circuit, 232 . . . switching circuit, 250 . . . bridge circuit, 251 . . . first bridge fixed resistor, 252 . . . second bridge fixed resistor, 253 . . . third bridge fixed resistor, 260 . . . amplification circuit.

The invention claimed is:

1. A gas detector comprising:

a heat generation resistor which is disposed in a to-be-detected atmosphere and whose resistance changes with a change in the temperature of the heat generation resistor;

a Wheatstone bridge circuit in which a first side including the heat generation resistor and a first resistor section connected in series and a second side including a second resistor section and a third resistor section connected in series are connected in parallel;

a bridge control section which controls the state of supply of electricity to the Wheatstone bridge circuit in such a manner that the Wheatstone bridge circuit becomes a balanced state; and a computation section which computes the concentration of a specific gas in the to-be-detected atmosphere, wherein the bridge control section includes an operational amplifier having an output terminal and two input terminals and controls the state of supply of electricity to the Wheatstone bridge circuit in accordance with the output of the operational amplifier in such a manner that a potential difference between the two input terminals of the operational amplifier becomes zero;

the Wheatstone bridge circuit is configured in such a manner that one of connection points where the first side and the second side are connected together serves as a reference point connected to one side of the bridge control section which becomes a low potential side when the bridge control section applies a voltage to the Wheatstone bridge circuit, the other of the connection points serves as a high potential point connected to the other side of the bridge control section which becomes a high potential side when the bridge control section applies the voltage to the Wheatstone bridge circuit, a connection point where the first resistor section and the heat generation resistor are connected together serves as a first potential point connected to one input terminal of the operational amplifier, and a connection point where the second resistor section and the third resistor section are connected together serves as a second potential point connected to the other input point of the operational amplifier;

the first resistor section has a characteristic such that a ratio of a change in the resistance due to deterioration with elapse of time or deterioration caused by an environmental load is small as compared with those of the second resistor section and the third resistor section; and the computation section comprises:

a gas concentration computation section which computes the concentration of the specific gas in the to-be-detected atmosphere through use of at least a voltage between opposite ends of the heat generation resistor detected on the basis of the potential at the first potential point, a reference judgment value storage section which stores a reference judgment value determined on the basis of a reference top potential which is a potential at the high potential point serving as a reference and a reference intermediate potential which is a potential at the first potential point or the second potential point serving as a reference, a detection-time judgment value computation section which computes a detection-time judgment value on the basis of a detection-time top potential which is a potential at the high potential point and a detection-time potential which is a potential at the first potential point or the second potential point at the time when gas detection is performed by the gas detector, and a deterioration judgment section which judges a deteriorated state of at least one of the second resistor section and the third resistor section on the basis of the reference judgment value and the detection-time judgment value.

2. The gas detector as claimed in claim 1, wherein the computation section includes an obtainment section which obtains the potential at the first potential point, and the potential at the first potential point obtained by the obtainment section is used for the computation of the concentration of the specific gas by the gas concentration computation section and the computation of the detection-time judgment value by the detection-time judgment value computation section.

3. The gas detector as claimed in claim 1, wherein the computation section includes a reference judgment value computation section which computes the reference judgment value on the basis of the reference top potential and the reference intermediate potential.

4. A gas detector comprising:

a heat generation resistor which is disposed in a to-be-detected atmosphere and whose resistance changes with a change in the temperature of the heat generation resistor;

a Wheatstone bridge circuit in which a first side including the heat generation resistor and a first resistor section connected in series and a second side including a second resistor section and a third resistor section connected in series are connected in parallel;

a bridge control section which controls the state of supply of electricity to the Wheatstone bridge circuit in such a manner that the Wheatstone bridge circuit becomes a balanced state; and a computation section which computes the concentration of a specific gas in the to-be-detected atmosphere, wherein the bridge control section includes an operational amplifier having an output terminal and two input terminals and controls the state of supply of electricity to the Wheatstone bridge circuit in accordance with the output of the operational amplifier in such a manner that a potential difference between the two input terminals of the operational amplifier becomes zero;

the Wheatstone bridge circuit is configured in such a manner that one of connection points where the first side and the second side are connected together serves as a reference point connected to one side of the bridge control section which becomes a low potential side when the bridge control section applies a voltage to the Wheatstone bridge circuit, the other of the connection points serves as a high potential point connected to the other side of the bridge control section which becomes a high potential side when the bridge control section applies the voltage to the Wheatstone bridge circuit, a connection point where the first resistor section and the heat generation resistor are connected together serves as a first potential point connected to one input terminal of the operational amplifier, and a connection point where the second resistor section and the third resistor section are connected together serves as a second potential point connected to the other input point of the operational amplifier;

the first resistor section has a characteristic such that a ratio of a change in the resistance due to deterioration with elapse of time or deterioration caused by an environmental load is small as compared with those of the second resistor section and the third resistor section; and the computation section comprises:

a gas concentration computation section which computes the concentration of the specific gas in the to-be-detected atmosphere through use of at least a voltage between opposite ends of the heat generation resistor detected on the basis of the potential at the first potential point, a reference judgment value storage section which stores a reference judgment value determined on the basis of a reference top potential which is a potential at the high potential point serving as a reference and a reference intermediate potential which is a potential at the first potential point or the second potential point serving as a reference, a detection-time judgment value computation section which computes a detection-time judgment value on the basis of a detection-time top potential which is a potential at the high potential point and a detection-time potential which is a potential at the first potential point or the second potential point at the time when gas detection is performed by the gas detector, and a voltage correction section which corrects the voltage between the opposite ends of the heat generation resistor on the basis of the reference judgment value and the detection-time judgment value.

5. The gas detector as claimed in claim 4, wherein the computation section includes a deterioration judgment section which judges a deteriorated state of at least one of the second resistor section and the third resistor section on the basis of the reference judgment value and the detection-time judgment value.

6. The gas detector as claimed in claim 4, further comprising a temperature measurement resistor whose resistance changes with a change in an environmental temperature which is the temperature of the to-be-detected atmosphere, wherein the gas concentration computation section computes the concentration of the specific gas through use of not only the voltage between the opposite ends of the heat generation resistor but also the environmental temperature detected through use of the temperature measurement resistor.

7. The gas detector as claimed in claim 4, wherein the computation section includes an obtainment section which obtains the potential at the first potential point, and the potential at the first potential point obtained by the obtainment section is used for the computation of the concentration of the specific gas by the gas concentration computation section and the computation of the detection-time judgment value by the detection-time judgment value computation section.

8. The gas detector as claimed in claim 4, wherein the computation section includes a reference judgment value computation section which computes the reference judgment value on the basis of the reference top potential and the reference intermediate potential.

9. A non-transitory computer readable medium comprising a program which is configured to control a gas detector comprising:

a heat generation resistor which is disposed in a to-be-detected atmosphere and whose resistance changes with a change in the temperature of the heat generation resistor;

a Wheatstone bridge circuit in which a first side including the heat generation resistor and a first resistor section connected in series and a second side including a second resistor section and a third resistor section connected in series are connected in parallel;

a bridge control section which controls the state of supply of electricity to the Wheatstone bridge circuit in such a manner that the Wheatstone bridge circuit becomes a balanced state; and a computation section which computes the concentration of a specific gas in the to-be-detected atmosphere, wherein the bridge control section includes an operational amplifier having an output terminal and two input terminals and controls the state of supply of electricity to the Wheatstone bridge circuit in accordance with the output of the operational amplifier in such a manner that a potential difference between the two input terminals of the operational amplifier becomes zero;

the Wheatstone bridge circuit is configured in such a manner that one of connection points where the first side and the second side are connected together serves as a reference point connected to one side of the bridge control section which becomes a low potential side when the bridge control section applies a voltage to the Wheatstone bridge circuit, the other of the connection points serves as a high potential point connected to the other side of the bridge control section which becomes a high potential side when the bridge control section applies the voltage to the Wheatstone bridge circuit, a connection point where the first resistor section and the heat generation resistor are connected together serves as a first potential point connected to one input terminal of the operational amplifier, and a connection point where the second resistor section and the third resistor section are connected together serves as a second potential point connected to the other input point of the operational amplifier;

the first resistor section has a characteristic such that a ratio of a change in the resistance due to deterioration with elapse of time or deterioration caused by an environmental load is small as compared with those of the second resistor section and the third resistor section, wherein the program is configured to cause the computation section to comprise:

a gas concentration computation section which computes the concentration of the specific gas in the to-be-detected atmosphere through use of at least a voltage between opposite ends of the heat generation resistor detected on the basis of the potential at the first potential point, a reference judgment value storage section which stores a reference judgment value determined on the basis of a reference top potential which is a potential at the high potential point serving as a reference and a reference intermediate potential which is a potential at the first potential point or the second potential point serving as a reference, a detection-time judgment value computation section which computes a detection-time judgment value on the basis of a detection-time top potential which is a potential at the high potential point and a detection-time potential which is a potential at the first potential point or the second potential point at the time when gas detection is performed by the gas detector, and a deterioration judgment section which judges a deteriorated state of at least one of the second resistor section and the third resistor section on the basis of the reference judgment value and the detection-time judgment value.

10. A non-transitory computer readable medium comprising a program which is configured to control a gas detector comprising:

a heat generation resistor which is disposed in a to-be-detected atmosphere and whose resistance changes with a change in the temperature of the heat generation resistor;

a Wheatstone bridge circuit in which a first side including the heat generation resistor and a first resistor section connected in series and a second side including a second resistor section and a third resistor section connected in series are connected in parallel;

a bridge control section which controls the state of supply of electricity to the Wheatstone bridge circuit in such a manner that the Wheatstone bridge circuit becomes a balanced state; and a computation section which computes the concentration of a specific gas in the to-be-detected atmosphere, wherein the bridge control section includes an operational amplifier having an output terminal and two input terminals and controls the state of supply of electricity to the Wheatstone bridge circuit in accordance with the output of the operational amplifier in such a manner that a potential difference between the two input terminals of the operational amplifier becomes zero;

the Wheatstone bridge circuit is configured in such a manner that one of connection points where the first side and the second side are connected together serves as a reference point connected to one side of the bridge control section which becomes a low potential side when the bridge control section applies a voltage to the Wheatstone bridge circuit, the other of the connection points serves as a high potential point connected to the other side of the bridge control section which becomes a high potential side when the bridge control section applies the voltage to the Wheatstone bridge circuit, a connection point where the first resistor section and the heat generation resistor are connected together serves as a first potential point connected to one input terminal of the operational amplifier, and a connection point where the second resistor section and the third resistor section are connected together serves as a second potential point connected to the other input point of the operational amplifier;

the first resistor section has a characteristic such that a ratio of a change in the resistance due to deterioration with elapse of time or deterioration caused by an environmental load is small as compared with those of the second resistor section and the third resistor section, wherein the program is configured to cause the computation section to comprise:

a gas concentration computation section which computes the concentration of the specific gas in the to-be-detected atmosphere through use of at least a voltage between opposite ends of the heat generation resistor detected on the basis of the potential at the first potential point, a reference judgment value storage section which stores a reference judgment value determined on the basis of a reference top potential which is a potential at the high potential point serving as a reference and a reference intermediate potential which is a potential at the first potential point or the second potential point serving as a reference, a detection-time judgment value computation section which computes a detection-time judgment value on the basis of a detection-time top potential which is a potential at the high potential point and a detection-time potential which is a potential at the first potential point or the second potential point at the time when gas detection is performed by the gas detector, and a voltage correction section which corrects the voltage between the opposite ends of the heat generation resistor on the basis of the reference judgment value and the detection-time judgment value.

* * * * *